(12) United States Patent
Berger et al.

(10) Patent No.: US 10,446,768 B2
(45) Date of Patent: *Oct. 15, 2019

(54) SELF-ASSEMBLED PEPTIDE NUCLEIC ACIDS

(71) Applicant: Ramot at Tel-Aviv University Ltd., Tel-Aviv (IL)

(72) Inventors: Or Berger, Tiberias (IL); Lihi Adler-Abramovich, Herzlia (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/648,524

(22) Filed: Jul. 13, 2017

(65) Prior Publication Data

US 2017/0309842 A1  Oct. 26, 2017

Related U.S. Application Data

(63) Continuation of application No. 14/888,468, filed as application No. PCT/IL2014/050398 on May 1, 2014, now Pat. No. 9,741,948.

(60) Provisional application No. 61/818,496, filed on May 2, 2013.

(51) Int. Cl.
  *C07K 14/00* (2006.01)
  *B82Y 30/00* (2011.01)
  *H01L 51/00* (2006.01)
  *C09K 11/06* (2006.01)
  *H01L 51/50* (2006.01)

(52) U.S. Cl.
  CPC ........ *H01L 51/0093* (2013.01); *C07K 14/003* (2013.01); *C09K 11/06* (2013.01); *C09K 2211/145* (2013.01); *C09K 2211/1466* (2013.01); *H01L 51/5012* (2013.01)

(58) Field of Classification Search
  None
  See application file for complete search history.

(56) References Cited

U.S. PATENT DOCUMENTS 8,309,514 B2  11/2012  Zhao et al.
2003/0232355 A1  12/2003  Norden et al.
(Continued)

FOREIGN PATENT DOCUMENTS

WO  WO 2004/052773  6/2004
WO  WO 2004/060791  7/2004
(Continued)

OTHER PUBLICATIONS

Haaima et al, New. J. Chem, vol. 23, pp. 833-840. (Year: 1999).*
(Continued)

*Primary Examiner* — Robert T. Crow

(57) ABSTRACT

Ordered (e.g., self-assembled) structures, arranged from peptide nucleic acids and/or analogs thereof, are disclosed. The peptide nucleic acids forming the ordered structures comprise from 1 to 10 PNA backbone units, at least one comprising a guanine nucleobase or an analog thereof. Processes of generating the ordered structures, uses thereof and articles-of manufacturing, devices and systems containing same are also disclosed.

17 Claims, 15 Drawing Sheets
(6 of 15 Drawing Sheet(s) Filed in Color)

(56) References Cited

U.S. PATENT DOCUMENTS

2004/0137469 A1    7/2004   Casale et al.
2016/0164010 A1    6/2016   Berger et al.

FOREIGN PATENT DOCUMENTS

WO    WO 2007/043048    4/2007
WO    WO 2014/178057    11/2014

OTHER PUBLICATIONS

"Hanging Drop Vapor Diffusion Crystallization," Hampton Research, pp. 1-2; 1991-2017 [retrieved on Nov. 29, 2017]. Retrieved from the Internet: <URL: hamptonresearch.com/documents/growth_101/3.pdf>. (Year: 2019).*
Communication Pursuant to Article 94(3) EPC dated Aug. 17, 2017 From the European Patent Office Re. Application No. 14791898.1. (3 Pages).
International Preliminary Report on Patentability dated Nov. 12, 2015 From the International Bureau of WIPO Re. Application No. PCT/IUL2014/050398.
International Search Report and the Written Opinion dated Aug. 13, 2014 From the International Searching Authority Re. Application No. PCT/IUL2014/050398.
Notice of Allowance dated Apr. 12, 2017 From the US Patent and Trademark Office Re. U.S. Appl. No. 14/888,468. (11 pages).
Official Action dated Sep. 26, 2016 From the US Patent and Trademark Office Re. U.S. Appl. No. 14/888,468.
Restriction Official Action dated Apr. 29, 2016 From the US Patent and Trademark Office Re. U.S. Appl. No. 14/888,468.
Supplementary European Search Report and the European Search Opinion dated Dec. 7, 2016 From the European Patent Office Re. Application No. 14791898.1. (6 Pages).
Achim et al. "Peptide Nucleic Acids", Wiley Encyclopedia of Chemical Biology, p. 1-10, 2008.
Becker et al. "Peptide Nucleic Acid Films and Capsules: Assembly and Enzymatic Degradation", Macromolecular Bioscience, XP002764646, 10(4): 489-495, May 14, 2010. Table 1.
Becker et al. "Peptide Nucleic Acid Films and Capsules: Assembly and Enzymatic Degradation", Macromolecular Bioscience, XP002764646, 10(5): 488-495, May 14, 2010.
Bonifazi et al. "Peptide Nucleic Acids in Materials Science", Artificial DNA: PNA & XNA, 3(3): 112-122, Jul.-Dec. 2012.
Briones et al. "Structural and Functional Characterization of Self-Assembled Monolayers of Peptide Nucleic Acids and Its Interaction With Complementary DNA", Journal of Molecular Catalysis A: Chemical, 228(1): 131-136, 2005.
Cao et al. "Synthesis and Characterization of Thermoreversible Biopolymer Microgels Based on Hydrogen Bonded Nucleobase Pairing", Journal of the American Chemical Society, JACS, 125(34): 10250-10256, 2003.
Guler et al. "Enhanced Oligonucleotide Binding to Self-Assembled Nanofibers", Bioconjugate Chemistry, 16(3): 501-503, 2005.
Harris et al. "PNA Encoding (PNA=Peptide Nucleic Acid): From Solution-Based Libraries to Organized Microarrays", Chemistry—A European Journal, 11(23): 6792-6801, 2005.
He et al. "Hierarchical Self-Assembly of DNA Into Symmetric Supramolecular Polyhedra", Nature, 452(7184): 198-201, Mar. 13, 2008.
Kerman et al. "Peptide Nucleic Acid-Modified Carbon Nanotube Field-Effect Transistor for Ultra-Sensitive Real-Time Detection of DNA Hybridization", NanoBiotechnology, 1(1): 65-70, Mar. 2005.
Liu et al. "Light-Directed Synthesis of Peptide Nucleic Acids (PNAs) Chips", Biosensors and Bioelectronics, 22(12): 2891-2897, 2007.
Lukeman et al. "Two Dimensional PNA/DNA Arrays: Estimating the Helicity of Unusual Nucleic Acid Polymers", Chemical Communications, 2004(15): 1694-1695, 2004.
Lundin et al. "Biological Activity and Biotechnology Aspects of Peptide Nucleic Acid", Advances in Genetic, 56: 1-51, 2006.
Maehashi et al. "Ultrasensitive Detection of DNA Hybridization Using Carbon Nanotube Field-Effect Transistors", Japanese Journal of Applied Physics, 43(12A): L1558-L1560, 2004.
Mateo-Marti et al. "A DNA Biosensor Based on Peptide Nucleic Acids on Gold Surfaces", Biosensors and Bioelectronics, 22(9): 1926-1932, 2007.
Mateo-Marti et al. "Do Peptide Nucleic Acids Form Self-Assembled Monolayers on Pyrite Surfaces?", Surface Science, 601(18): 4195-4199, 2007.
Mateo-Marti et al. "Self-Assembled Monolayers of Peptide Nucleic Acids on Gold Surfaces: A Spectroscopic Study", Langmuir, 21(21): 9510-9517, 2005.
Miyake et al. "MercuryII-Mediated Formation of Thymine-HgII-Thymine Base Pairs in DNA Duplexes", Journal of the American Chemical Society, JACS, 128(7): 2172-2173, 2006.
Ono et al. "Specific Interactions Between Silver(I) Ions and Cytosine-Cytosine Pairs in DNA Duplexes", Chemical Communications, 2008(39): 4825-4827, 2008.
Phan et al. "Human Telomeric DNA: G-Quadruplex, I-Motif and Watson-Crick Double Helix", Nucleic Acids Research, 30(21): 4618-4625, 2002.
Rajendra et al. "The Binding of Single-Stranded DNA and PNA to Single-Walled Carbon Nanotubes Probed by Flow Linear Dichroism", Chemistry—A European Journal, 11(16): 4841-4847, 2005.
Rasmussen et al. "Crystal Structure of a Peptide Nucleic Acid (PNA) Duplex at 1.7 A Resolution", Nature Structural Biology, 4(2): 98-101, Feb. 1997.
Reches et al. "Casting Metal Nanowires Within Discrete Self-Assembled Peptide Nanotubes", Science, XP002276672, 300(5619): 625-627, Apr. 25, 2003.
Seeman "DNA Engineering and Its Application to Nanotechnology", Trends in Biotechnology, TIBTECH, 17(11): 437-443, Nov. 1999.
Singh et al. "Application of Peptide Nucleic Acid Towards Development of Nanobiosensor Arrays", 79(2): 153-161, 2010.
Williams et al. "Carbon Nanotubes With DNA Recognition", Nature, 420: 761, Dec. 19/26, 2002.
Winfree et al. "Design and Self-Assembly of Two Dimensional DNA Crystals", Nature, 394(6693): 539-544, Aug. 6, 1998.

* cited by examiner

|   | A | C | G | T |
|---|---|---|---|---|
| A | AA | AC | AG | AT |
| C | CA | CC | CG | CT |
| G | GA | GC | GG | GT |
| T | TA | TC | TG | TT |

FIG. 2A

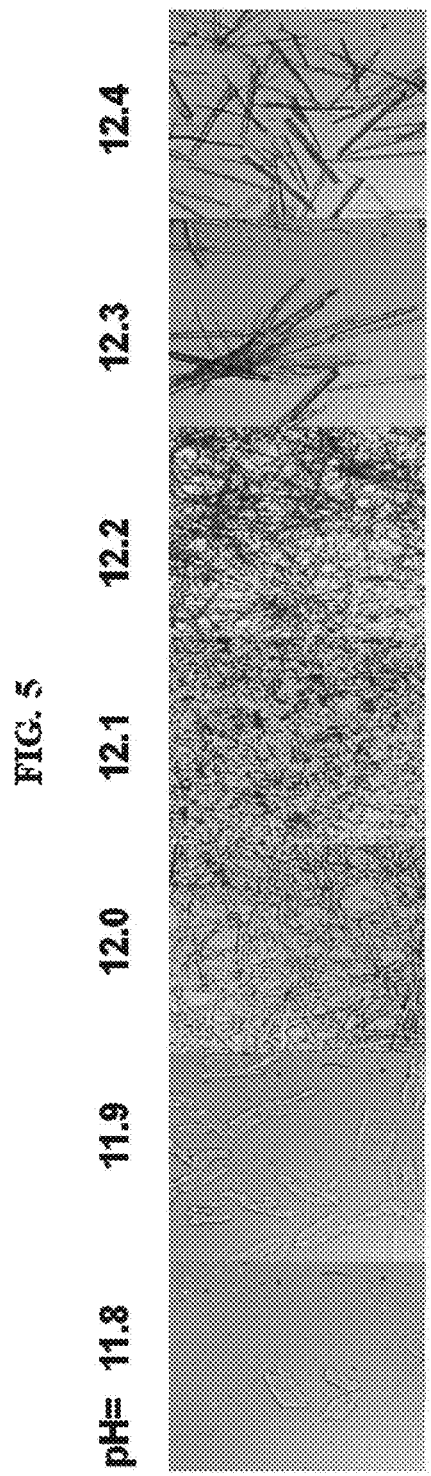

SELF-ASSEMBLED PEPTIDE NUCLEIC ACIDS

RELATED APPLICATIONS

This application is a continuation of U.S. patent application Ser. No. 14/888,468 filed on Nov. 2, 2015, which is a National Phase of PCT Patent Application No. PCT/IL2014/050398 having International Filing Date of May 1, 2014, which claims the benefit of priority from U.S. Provisional Patent Application No. 61/818,496 filed on May 2, 2013.

The contents of the above applications are all incorporated by reference as if fully set forth herein in their entirety.

FIELD AND BACKGROUND OF THE INVENTION

The present invention, in some embodiments thereof, relates to material science and, more particularly, but not exclusively, to nano- and micro-structures composed of self-assembled peptide nucleic acids (PNAs), to processes of generating same and to uses thereof.

Molecular self-assembly is the spontaneous organization of molecular units into ordered structures as a result of local interactions among the molecules themselves, without any external intervention. The concept of self-assembly is a widely applied approach in the field of nanotechnology for the bottom-up fabrication of novel nanoscopic and macroscopic elements from natural or synthetic building blocks.

Peptide building blocks have been widely used in the past decade or so for forming well-organized assemblies. The arrangement into ordered structures involves a combination of non-covalent interactions such as van der Waals, electrostatic, hydrophobic and aromatic π-stacking interactions as well as hydrogen and coordination bonds. The synergy between these weak individual forces often leads to the formation of ordered structures with notable morphological, mechanical and other physical features.

Structural DNA nanotechnology is derived from the specificity of the hydrogen bonding interactions between complementary Watson-Crick base pairs, which enables the recognition and highly selective binding of complementary strands. These features were recognized as useful for the construction of ordered structures via self-assembly and have been exploited to rationally design various structures including nanowires, nanogrids and three-dimensional well-ordered shapes. See, for example, Winfree et al. Nature, 1998. 394(6693): p. 539-544; He et al. Nature, 2008. 452(7184): p. 198-201; and Seeman, N.C., Trends in biotechnology, 1999. 17(11): p. 437-443.

Both peptides and DNA are susceptible to enzymatic degradation and are also typically characterized by chemical sensitivity to temperatures and pH. These features limit the use of peptide- and DNA-based assemblies.

Peptide nucleic acid (PNA) is an artificially synthesized polymer that was first described by Peter Nielsen's and Ole Buchardt's research groups in 1992. In its basic form, it is an oligonucleotide analog in which the phosphate ribose ring of DNA is replaced by a polyamide backbone composed of repeating N-(2-aminoethyl)glycine units linked by peptide bonds. Methylene carbonyl linkages connect between the central amine of the backbone and the various nucleobases. The configuration and the intramolecular distances between neighboring bases, as imposed by the peptide-like backbone, are equal to those in natural nucleic acids.

Background art FIG. 1 presents the general chemical structure of PNA, compared to that of DNA [Lundin et al. Advances in genetics, 2006. 56: p. 1-51].

PNAs have been used in the formation of ordered nano- and micro-sized self-assembled architectures, yet only as a template or as a conjugate to the self-assembled structure in order to gain specific recognition properties.

Thus, to date, PNAs are utilized in the context of material science mainly as a molecular probe for diagnostics and detection.

The following approaches have been employed in this regard: (1) PNA-based self-assembled monolayers on solid surfaces (nanoparticles or bulk materials) [see, for example, Harris, J. L. and N. Winssinger, Chemistry—a European Journal, 2005. 11(23): p. 6792-6801; Briones et al. Journal of Molecular Catalysis A: Chemical, 2005. 228(1): p. 131-136; Liu et al. Biosensors and Bioelectronics, 2007. 22(12): p. 2891-2897; Mateo-Marti et al. Biosensors and Bioelectronics, 2007. 22(9): p. 1926-1932; Mateo-Marti et al. Langmuir, 2005. 21(21): p. 9510-9517; Mateo-Marti et al. Surface Science, 2007. 601(18): p. 4195-4199; and Singh et al. Bioelectrochemistry, 2010. 79(2): p. 153-161]; (2) carbon nanotubes (CNTs) covalently and non-covalently conjugated to PNAs [Williams et al. Nature, 2002. 420(761): p. 38; Kerman et al. Nanobiotechnology, 2005. 1(1): p. 65-70; Maehashi et al. Japanese journal of applied physics, 2004. 43: p. 1558; and Rajendra et al. Chemistry—a European Journal, 2005. 11(16): p. 4841-4847]; and (3) self-organized nanostructures including fibers [Guler et al. Bioconjug Chem, 2005. 16(3): p. 501-503; two-dimensional arrays [Lukeman et al. Chemical Communications, 2004(15): p. 1694-1695]; microgels [Cao et al. Journal of the American Chemical Society, 2003. 125(34): p. 10250-10256]; and films and capsules [Becker et al. Macromolecular bioscience, 2010. 10(5): p. 488-495].

Additional background art includes Achim et al., "Peptide Nucleic Acids" in Wiley Encyclopedia of Chemical Biology, 2008, pp. 1-10, Bonifazi et al., Artificial DNA: PNA & XNA 3:3, 112-122, July-December 2012, and U.S. Pat. No. 8,309,514.

SUMMARY OF THE INVENTION

The present inventors have devised and successfully practiced ordered structures, at a nanometric and micrometric scale, formed via self-assembly of short PNAs. The present inventors have demonstrated that guanine (G)-containing PNA dimers self-assemble into diverse nano- and micro-structures.

The disclosed PNA-derived self-assembled structures exhibit the advantages associated with PNAs as delineated hereinabove, namely, high biological and chemical stability and high affinity to complementary nucleic acids with stable hybridization, combine nanobiotechnology and DNA nanotechnology features and can therefore be efficiently utilized in various nanotechnology, biotechnology and biomedicine applications, as described hereinbelow.

According to an aspect of some embodiments of the present invention there is provided a composition-of-matter comprising a plurality of peptide nucleic acids arranged to form an ordered nanometric or microscopic structure, each of the peptide nucleic acids independently comprising 1 to 10 backbone units, at least one of the backbone units comprises a guanine nucleobase or an analog thereof.

According to some embodiments of the present invention, each of the peptide nucleic acids independently comprises 2 to 6 of the backbone units.

According to some embodiments of the present invention, each of the peptide nucleic acids comprises 2 of the backbone units and is being a peptide nucleic acid dimer (PNA dimer).

According to some embodiments of the present invention, each of the peptide nucleic acid dimers is independently selected from the group consisting of AG, CG, GG, GA, GC, and GT.

According to some embodiments of the present invention, the ordered structure is selected from the group consisting of a ribbon-shaped structure, a plurality of ribbon-shaped structures similar to one another in shape and dimensions, a fibrillar structure or a plurality of fibrillar structures which are similar to one another in shape and dimensions, a spherical structure or a plurality of spherical structures, or a cluster or a plurality of clusters of spherical structures, a structure shaped as a sheet or a folded sheet or a plurality of folded sheets, which are similar to one another in shape and dimensions, a porous fractal structure or a plurality of fractal structures.

According to some embodiments of the present invention, each of the peptide nucleic acid dimers is AG, in some embodiments, the ordered structure is a ribbon-shaped micrometric structure.

According to some embodiments of the present invention, each of the peptide nucleic acid dimers is CG, and, in some embodiments, the ordered structure is a fibrillar micrometric structure.

According to some embodiments of the present invention, each of the peptide nucleic acid dimers is GG, and, in some embodiments, the ordered structure is a clustered spherical micrometric structure.

According to some embodiments of the present invention, each of the peptide nucleic acid dimers is GA, and, in some embodiments, the ordered structure is a micrometric/nanometric folded sheet structure.

According to some embodiments of the present invention, each of the peptide nucleic acid dimers is GC, and, in some embodiments, the ordered structure is a fibrillar micrometric structure. In some embodiments, the ordered structure exhibits a crystalline structure.

According to some embodiments of the present invention, each of the peptide nucleic acid dimers is GT and, in some embodiments, ordered structure is a fractal porous nanometric or micrometric structure.

According to some embodiments of the present invention, the ordered structure is generated by contacting the plurality of peptide nucleic acids with an aqueous solution under conditions which favor formation of the ordered structure.

According to some embodiments of the present invention, the contacting is performed at room temperature.

According to some embodiments of the present invention, the aqueous solution has a pH greater than 7.

According to some embodiments of the present invention, a concentration of the plurality of peptide nucleic acids in the aqueous solution ranges from about 10 mg/ml to 100 mg/ml.

According to some embodiments of the present invention, a concentration of the plurality of peptide nucleic acids in the aqueous solution is at least 50 mg/ml.

According to some embodiments of the present invention, a concentration of the plurality of peptide nucleic acids in the aqueous solution is at about 50 mg/ml.

According to some embodiments of the present invention, the composition-of-matter as described herein further comprises an aqueous solution.

According to some embodiments of the present invention, the aqueous solution comprises a buffer having pH greater than 7.

According to some embodiments of the present invention, the ordered structure is formed at an elongation rate of at least 1 micron per second.

According to some embodiments of the present invention, at least $10^9$ molecules of the PNAs organize into the ordered structure per second.

According to some embodiments of the present invention, the ordered structure exhibits an excitation wavelength-dependent fluorescence emission.

According to some embodiments of the present invention, the excitation wavelength ranges from 330 nm to 430 nm.

According to an aspect of some embodiments of the present invention there is provided a process of generating the composition-of-mater of any one of the embodiments described herein, the process comprising contacting the plurality of peptide nucleic acids with an aqueous solution under conditions which favor formation of the ordered structure.

According to some embodiments of the present invention, the contacting is performed at room temperature.

According to some embodiments of the present invention, a concentration of the peptide nucleic acids in the aqueous solution ranges from 10 mg/ml to 100 mg/ml.

According to some embodiments of the present invention, the concentration is about 50 mg/ml.

According to some embodiments of the present invention, the aqueous solution is an alkaline solution.

According to an aspect of some embodiments of the present invention there is provided a composition comprising the composition-of-matter of any one of the embodiments described herein, and a material being in association with the ordered structure.

According to some embodiments of the present invention, the material is selected from the group consisting of a conductor material, a semiconductor material, a thermoelectric material, a magnetic material, a light-emitting material, a labeling agent, a ligand, a nucleic acid, a nucleic acid intercalator, a polypeptide, a peptide, a biomineral, a polymer, an organic material, a therapeutically active agent and an agent capable of modifying surface properties.

According to an aspect of some embodiments of the present invention there is provided a use of the composition-of-matter of any one of the embodiments described herein, or of the composition described herein in the manufacture of an article-of-manufacture or a device.

According to an aspect of some embodiments of the present invention there is provided an article-of-manufacturing comprising the composition-of-matter of any one of the embodiments described herein, or the composition described herein.

According to some embodiments of the present invention, the article-of-manufacture or device is selected from the group consisting of a medicament (a nucleic acid probe, a biosensor, an electrical device, a semiconducting article or device, a thermoelectric article or device, a magnetic article, a light-emitting article or device, a polymeric article, a metallic article or device, and an article or device having activated surface.

According to an aspect of some embodiments of the present invention there is provided a light emitting system, comprising the composition-of-matter of any one of the embodiments described herein or the composition as described herein.

According to some embodiments of the present invention, the composition-of-matter generates light responsively to applied voltage.

According to some embodiments of the present invention, the composition-of-matter generates light responsively to applied heat.

According to some embodiments of the present invention, the composition-of-matter converts light responsively to excitation light interacting therewith.

According to an aspect of some embodiments of the present invention there is provided a utility system, comprising the light emitting system as described herein, wherein the utility system is selected from the group consisting of a laser system, an active OLED display layer, a backlight system for a display, an optical communication system, an illumination system, and an optical connector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 (Background Art) illustrates the basic structural difference and similarity between DNA and PNA, as adapted from Lundin et al. [Advances in genetics, 2006. 56: p. 1-51];

FIG. 2A presents the various combinations of PNA dimers synthesized and tested for formation of self-assembled structures. Highlighted in black are PNA dimers which formed well-ordered assembly under alkaline conditions. Highlighted in grey are PNA dimers which formed ordered assemblies upon drying the sample.

Figure 2B:
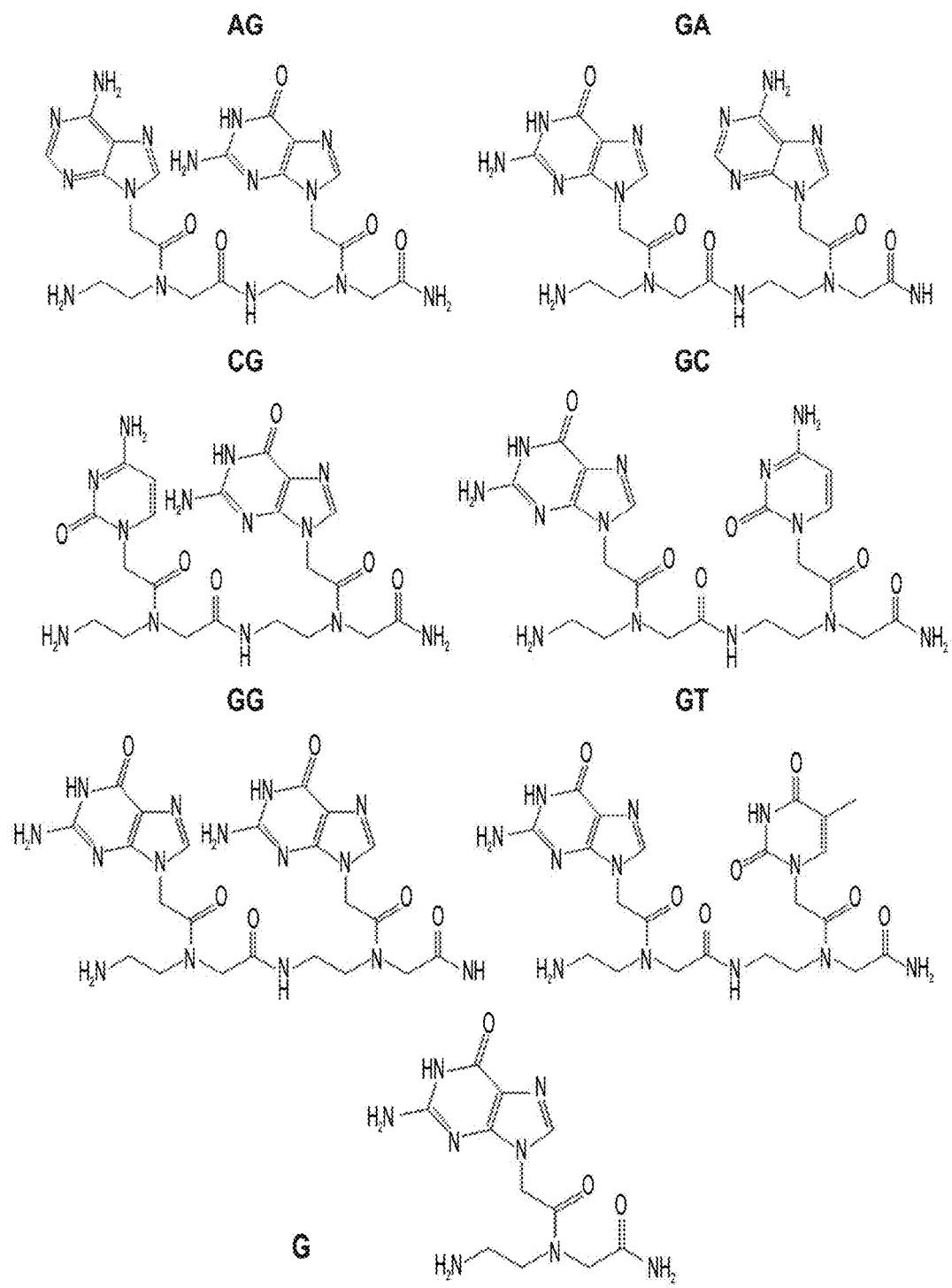

FIG. 2B illustrates the chemical structures of the assemblies-forming, guanine-containing PNA dimers, according to some embodiments of the present invention, and of guanine.

Figure 3A:
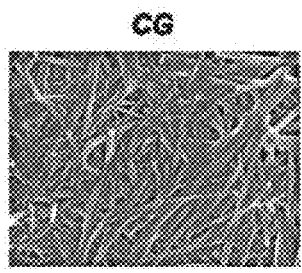
Figure 3B:
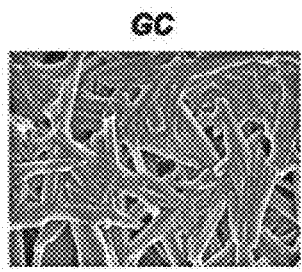
Figure 3C:
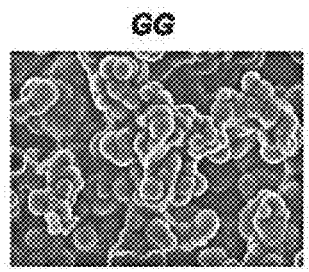
Figure 4A:
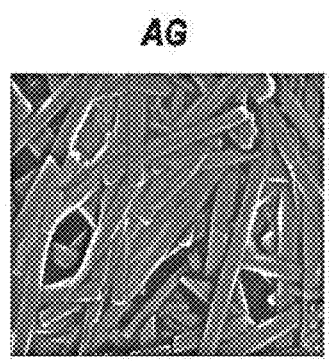
Figure 4B:
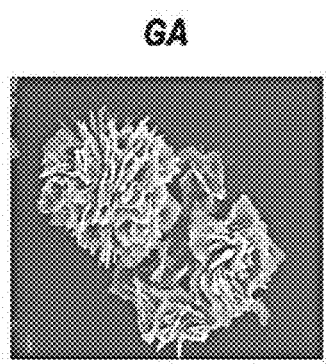
Figure 4C:
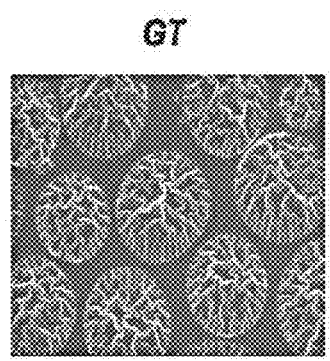
Figure 4D:
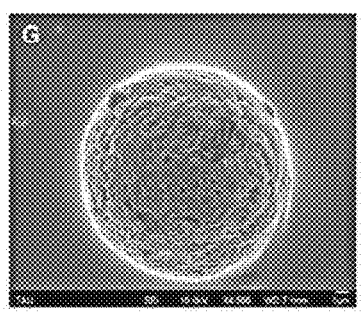

FIGS. 3A-3C present SEM micrographs of the ordered structures formed by contacting the di-PNA (PNA dimers) CG (FIG. 3A), GC (FIG. 3B) and GG (FIG. 3C) with a basic aqueous solution (bicine buffer or spermidine-containing aqueous solution) at PNA concentration of 50 mg/ml. SEM micrographs were taken upon diluting the basic solution to PNA concentration of 10 mg/ml. The bar size is 10 μm.

FIGS. 4A-4D present SEM micrographs of the structures formed by contacting the di-PNA (PNA dimers) AG (FIG. 4A), GA (FIG. 4B), GT (FIG. 4C), and the PNA monomer G (FIG. 4D) with a basic aqueous solution (bicine buffer or spermidine-containing aqueous solution) at PNA concentration of 50 mg/ml. SEM micrographs were taken upon diluting the basic solution to PNA concentration of 10 mg/ml. The bar size is 10 μm.

FIG. 5 presents light microscopy images of assemblies formed by GC di-PNA upon contacting the di-PNA with an aqueous solution with rising pH levels of disodium hydrogen phosphate buffer.

Figure 6A:
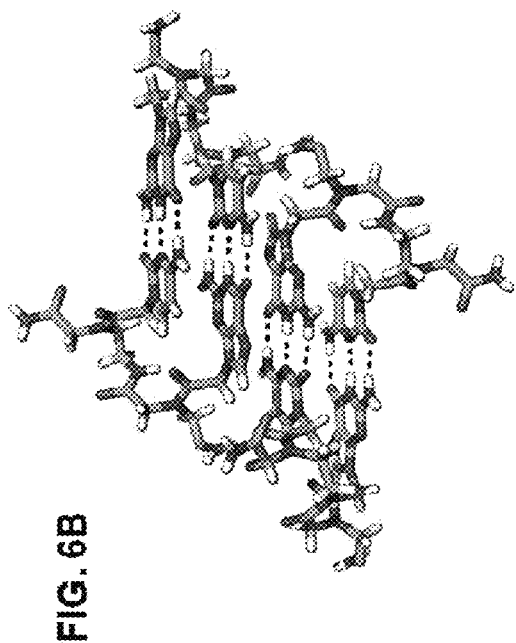
Figure 6B:
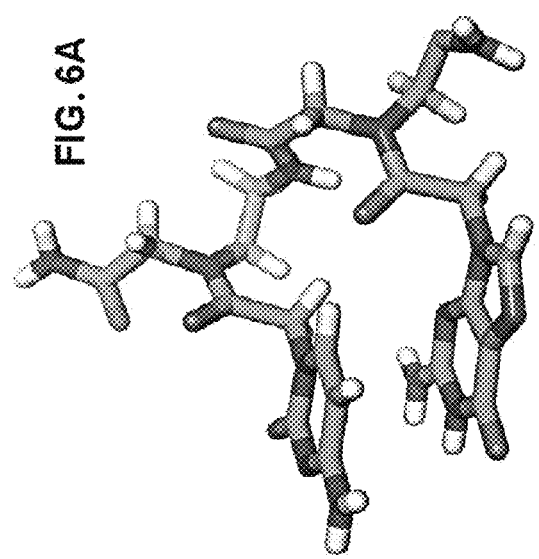
Figure 6C:
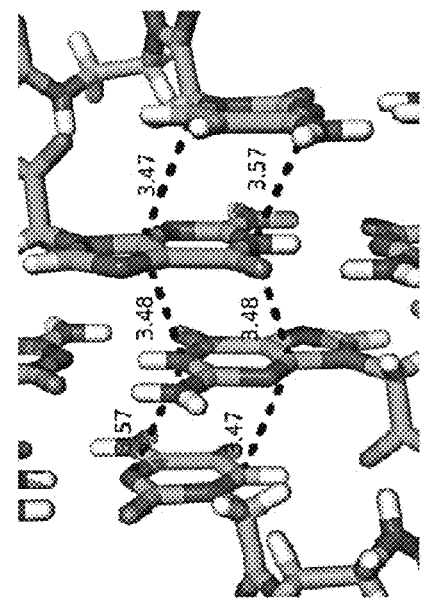
Figure 6D:
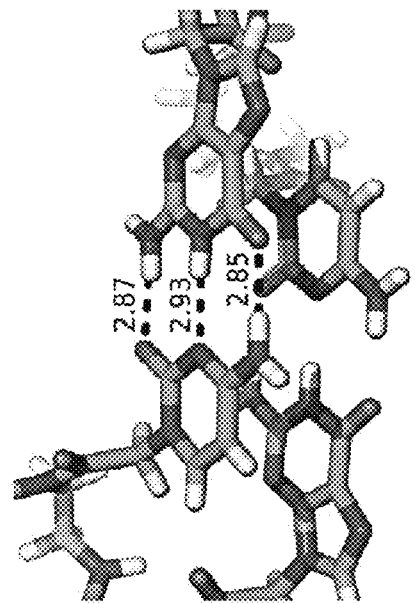
Figure 6F:
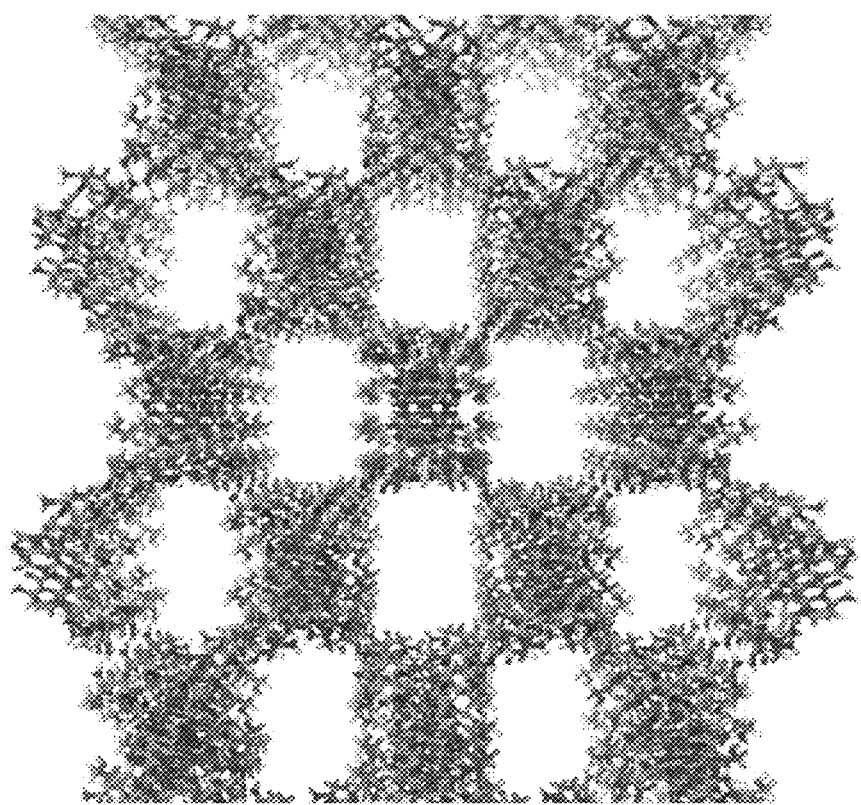

FIGS. 6A-6F present data obtained upon crystallization and single crystal structure determination of GC di-PNA building block. The molecular structure of a single GC di-PNA shows that the cytosine and guanine nucleobases form an intramolecular stacking interaction (FIG. 6A). Each molecule forms hydrogen bonds with a neighboring unit between the cytosine and guanine residues (FIG. 6B). The hydrogen bond length between symmetry related molecules is measured to be 2.85-2.93 Å (FIG. 6C). The bases are 3.5 Å apart (FIG. 6D). The di-PNA units are packed in an 'infinite' tilted stack through the crystal (FIG. 6E), which results in rectangular-shaped pores comprising over 50% of the crystal volume (FIG. 6F).

Figure 7A:
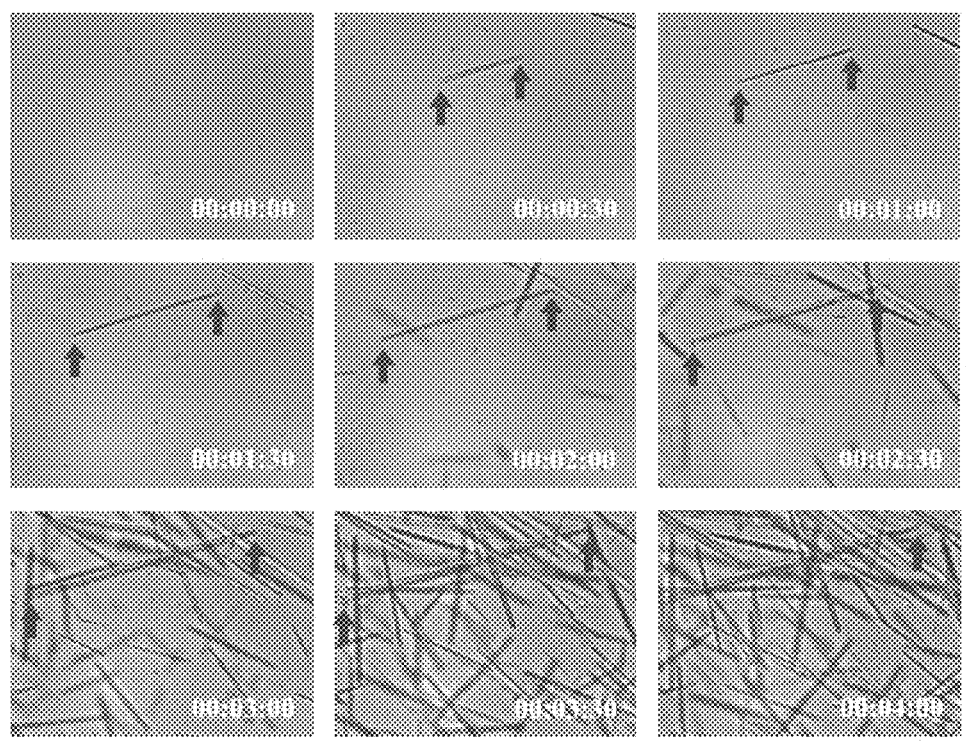
Figure 7B:
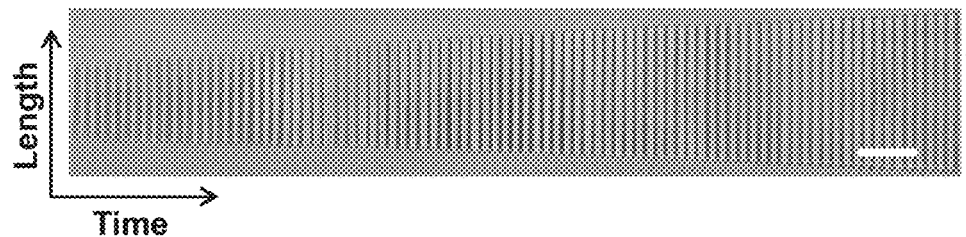
Figure 7C:
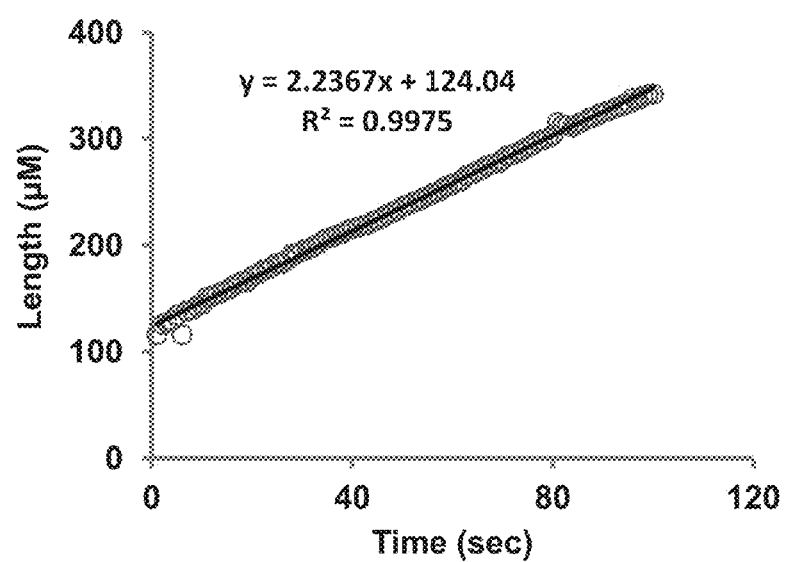

FIGS. 7A-7C present the assembly kinetics of GC di-PNA, and show 9 snapshots, captured every 30 minutes, upon deposition of single drop of a fresh solution of GC di-PNA structures (5 mg/ml) in 100 mM bicine buffer on a glass slide and monitoring over time using light microscopy (FIG. 7A), with the edges of a single elongating structure marked with a red arrow in each frame; Kymograph presenting the elongation of the same single structure between frames 26 to 112 made by a series of images of the structure as appears in each of the frames from left to right respectively (FIG. 7B), with the bar size being 30 μm; and a graph representation of the elongation rate (FIG. 7C), showing that the calculated elongation rate is 2.23 μm per second.

Figure 8A:
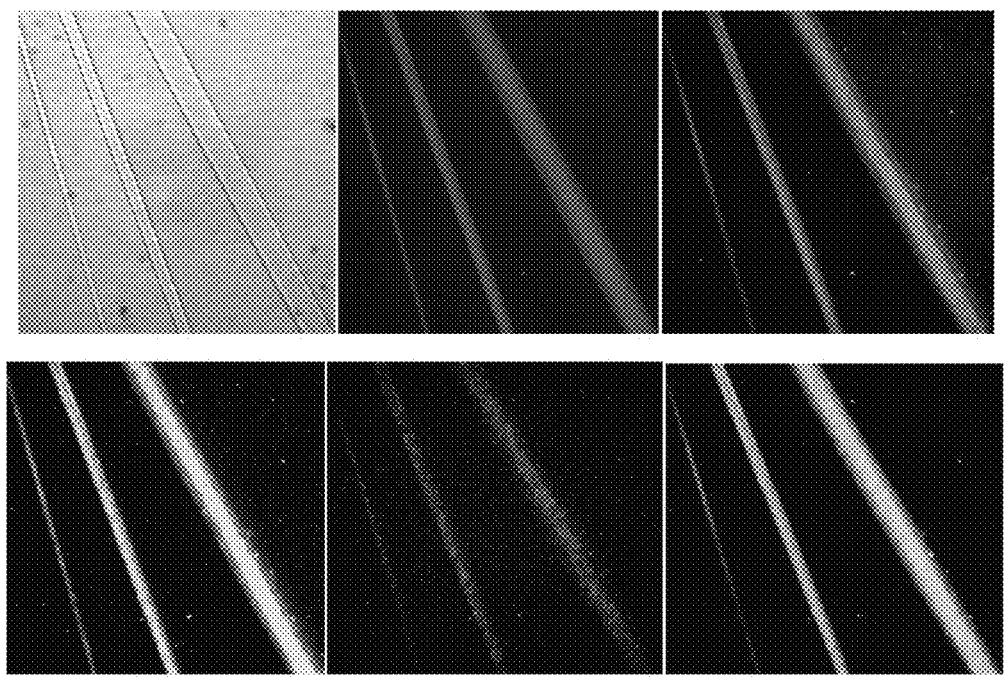
Figure 8B:
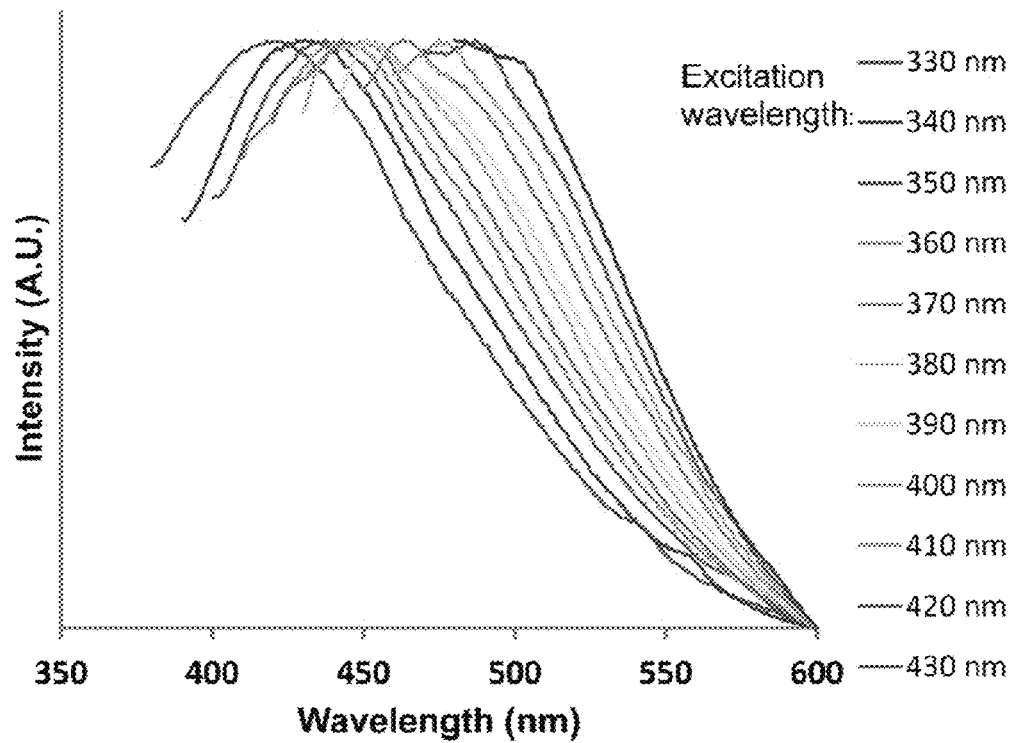
Figure 8C:
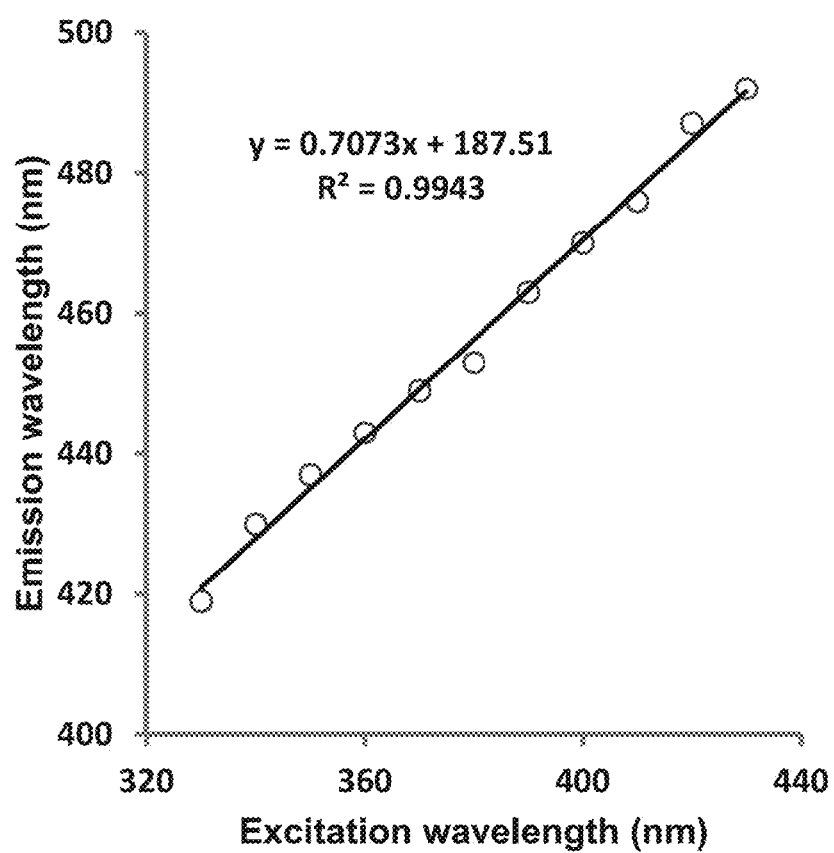

FIGS. 8A-8C present a bright-field and five fluorescence images of the same microscopic field of GC di-PNA structures prepared in bicine buffer, upon dilution to a 5 mg/ml concentration, with fluorescence images taken with the following excitation and emission filters: ex: 387 nm/em: 440 nm; ex: 485 nm/em: 525 nm; ex: 537 nm/em: 578 nm; ex: 560 nm/em: 607 nm; ex: 650 nm/em: 684 nm, from top to bottom respectively, and pseudo-colors representing corresponding emission color (FIG. 8A); Emission spectra of GC di-PNA assemblies at excitation wavelengths of 330, 340, 350, 360, 370, 380, 390, 400, 410, 420 and 430 nm, showing that the emission peak is shifted to the red with higher excitation wavelengths (FIG. 8B); and a graph representation of the relation between the excitation and emission wavelengths, showing a slope of 0.7, which suggests a dynamic Stokes shift.

Figure 9:
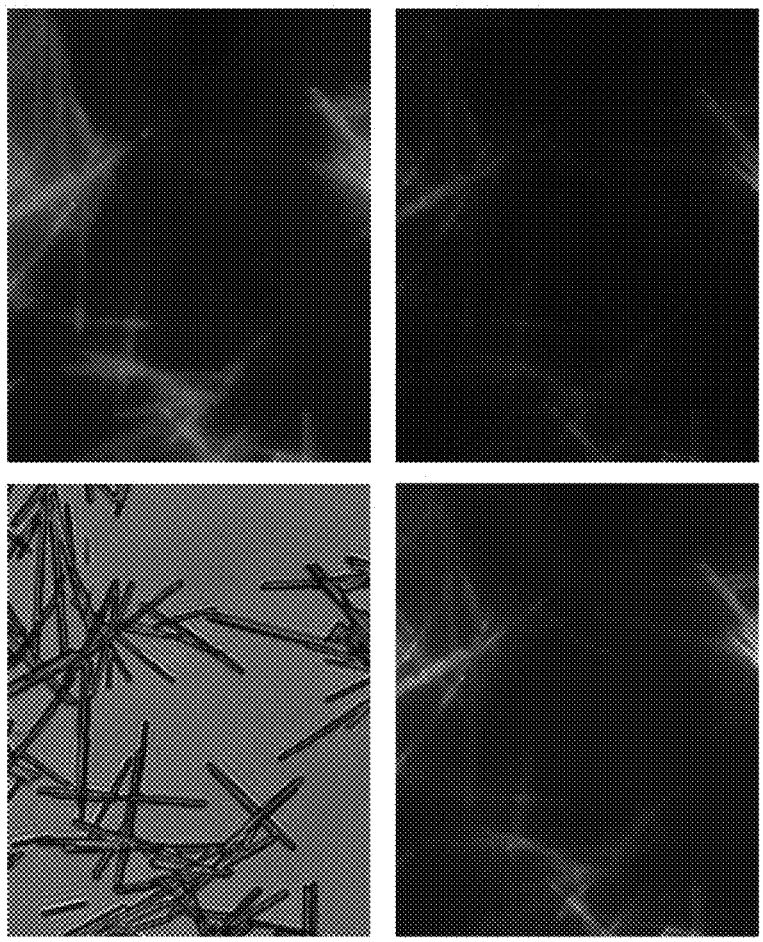

FIG. 9 presents a bright-field and three fluorescence images of the same microscopic field of CG di-PNA structures prepared in bicine buffer, upon dilution to 5 mg/ml concentration.

Figure 10A:
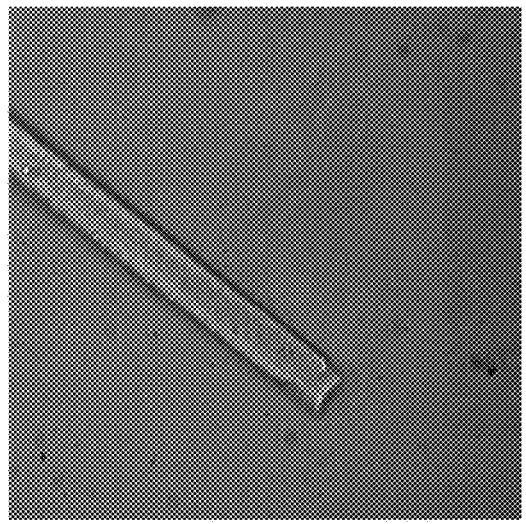
Figure 10B:
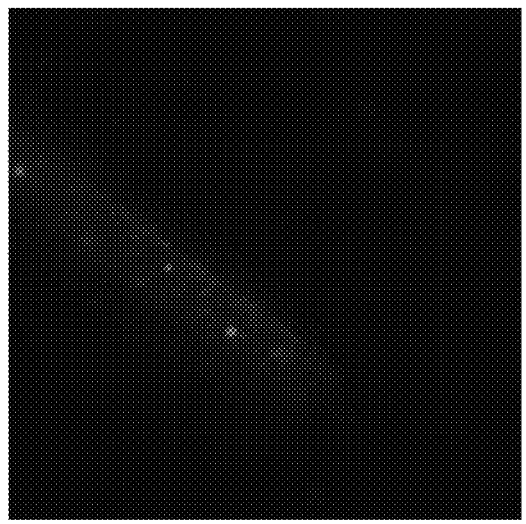

FIGS. 10A-10B present a bright-field (FIG. 10A) and fluorescence image (FIG. 10B) of a single GC assembly dyed with the intercalator YOYO-3 that exhibits red light emission when bound to nucleic acids.

Figure 11A:
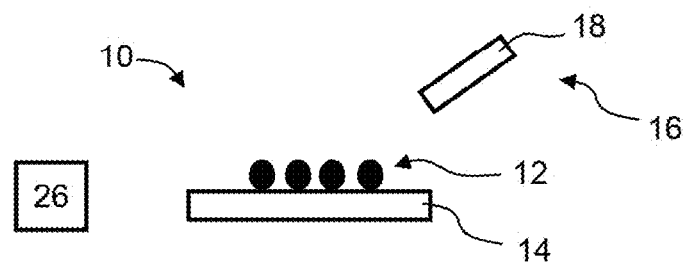
Figure 11B:
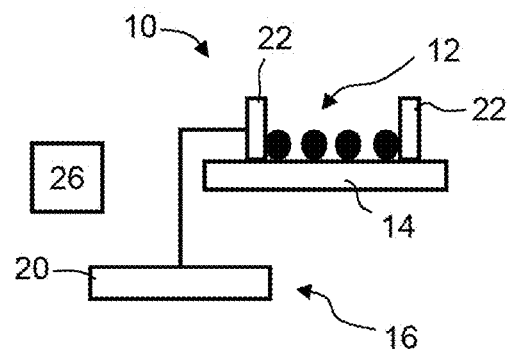
Figure 11C:
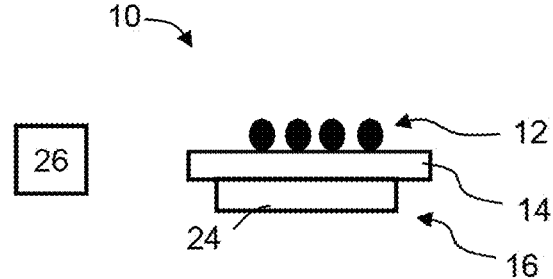

FIGS. 11A-11C are schematic illustrations of a light emitting system 10, according to some embodiments of the present invention.

Figure 12:
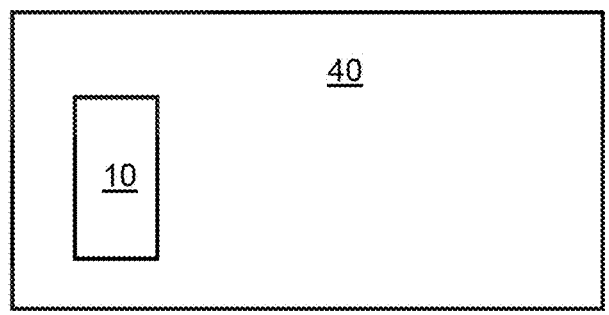

FIG. 12 is a schematic illustration of a utility system 40 according to various exemplary embodiments of the present invention.

Figure 13:
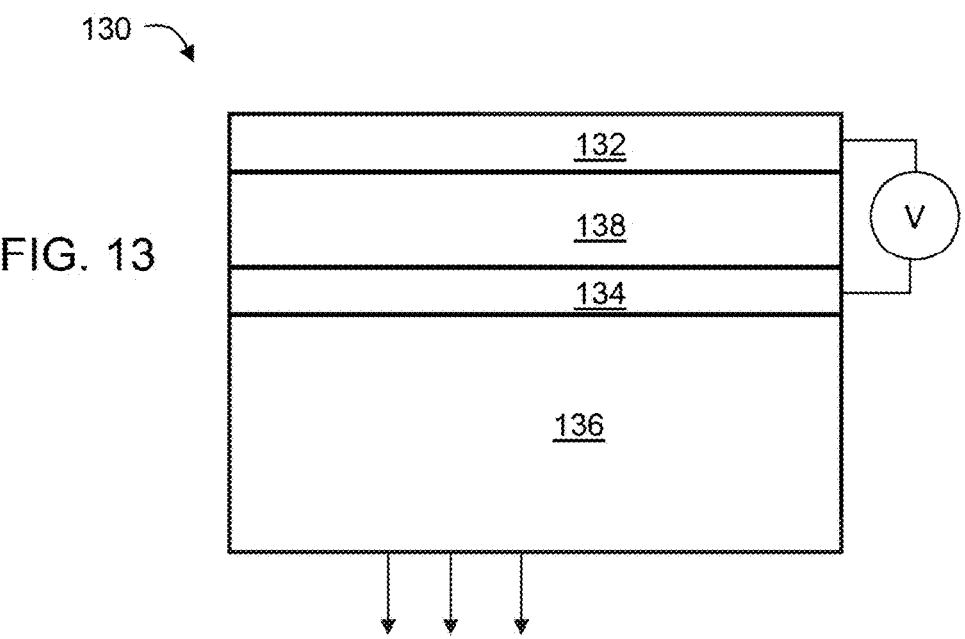

FIG. 13 is a more detailed illustration of an OLED 130, according to some embodiments of the present invention.

Figure 14:
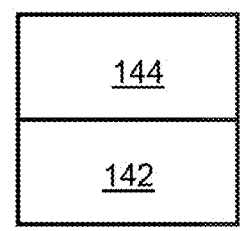

FIG. 14 is a schematic illustration of a light emitting system 140 in embodiments in which light conversion is employed.

Figure 15:
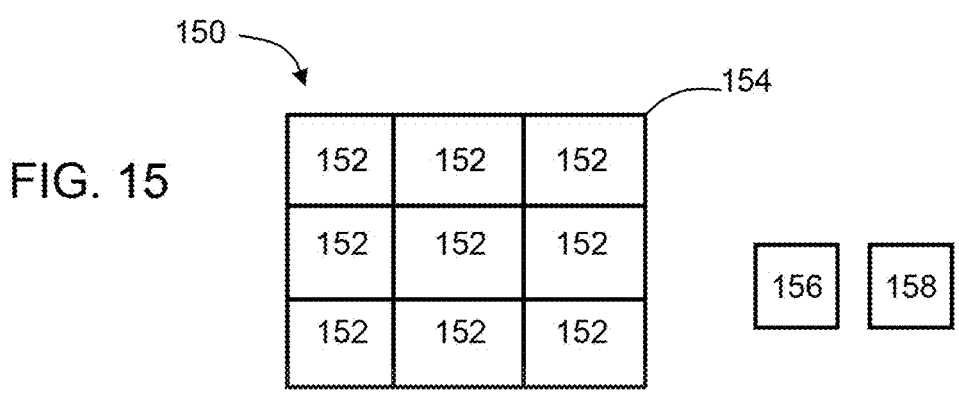

FIG. 15 is a schematic illustration of a display system 150, according to some embodiments of the present invention.

DESCRIPTION OF SPECIFIC EMBODIMENTS
OF THE INVENTION

The present invention, in some embodiments thereof, relates to material science and, more particularly, but not exclusively, to nano- and micro-structures composed of self-assembled peptide nucleic acids (PNAs), to processes of generating same and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, the two main branches of bionanotechnology are comprised of peptide- and DNA-based self-organizing systems. While peptide scaffolds offer robustness, chemical versatility, architectural flexibility as well as structural complexity, nucleic acid nanostructures are characterized by precise base-pairing complementarity and specific molecular recognition.

The present inventors have envisioned that building blocks that converge these two variant strategies may prove to be ideal for the fabrication of novel self-assembled materials, and have therefore conceived exploring the assembly of short PNA oligomers.

The use of PNAs offers the following advantages: PNA is able to bind complementary DNA or RNA in accordance to Watson-Crick base-pairing rules, with even greater affinity and specificity compared to binding of natural nucleic acids. The hybridization properties remain good even in high or low ion concentrations. The hybridization thermal stability of PNA/DNA duplex is higher than that of DNA/DNA due to the lack of charges in the backbone, compared to two negatively charged backbones which repulse one another. PNA also displays high bio-stability as it is resistant to degradation by proteases and nucleases.

While reducing the present invention to practice, PNA dimers (di-PNAs) of all 16 combinations of the four DNA nucleobases G, C, A and T, were synthesized and assayed for their ability to self-assemble into ordered structures (see, FIGS. 2A-2B). As demonstrated in the Examples section that follows, three guanine-containing di-PNAs: CG, GC, and GG formed ordered assemblies immediately (e.g., within a few minutes), and three other guanine-containing di-PNAs: AG, GA, and GT, formed ordered assemblies upon drying, as identified by electron microscopy (see, FIGS. 3A-3C and 4A-4D).

An exemplary X-ray crystal structure of the GC di-PNA at 0.95 Å resolution demonstrated the occurrence of both stacking interactions as well as Watson-Crick base-pairing (see, FIGS. 6A-6F). Analyzing the self-assembly kinetics while employing crystal structure formation revealed a very rapid organization of PNA dimers into ordered structures (see, FIGS. 7A-7C). Fluorescence studies of the structures revealed dynamic Stokes shift of the PNA-based assemblies and excitation-dependent emission that spans a wide region of the visible spectrum (see, FIGS. 8A-8C).

Thus, it has been demonstrated herein that PNA-containing building blocks may self-assemble into ordered structures, coordinated by both stacking interaction as well as Watson-Crick base-pairing. The ultrastructures show the combination of intramolecular organization together with ordered supramolecular arrangement. The structures were assembled into discrete and uniform entities, exhibiting very fast elongation kinetics. These structures exhibit excitation-dependent emission and dynamic Stokes shift which are unique for such organic supramolecular systems.

The novel PNA-based assemblies disclosed herein offer simplicity, prompt and efficient assembly and the availability of industry standard deposition methods such as physical vapor deposition, together with extended and tunable spectral properties and high molar absorptivity.

According to an aspect of some embodiments of the present invention there is provided a composition-of-matter comprising a plurality of peptide nucleic acids (PNAs), each of the peptide nucleic acids comprising 1 to 10 backbone units wherein at least one of these backbone units comprises a guanine nucleobase or an analog thereof.

In some embodiments, the plurality of peptide nucleic acids is arranged to form an ordered structure, as defined herein.

In some embodiments, the plurality of peptide nucleic acids self-assembles to form an ordered structure, as defined herein.

The Peptide Nucleic Acid and Backbone Units Thereof:

In any of the aspects and embodiments of the present invention, the terms "peptide nucleic acid", "PNA" and "PNA oligomers" are used interchangeably and encompass a monomer, comprising a single backbone unit, or an oligomer of 2-10 backbone units, as described herein.

Herein throughout, the phrase "backbone unit", which is also referred to as "PNA backbone unit" or "PNA monomer", and grammatical diversions thereof, describes a N-(2-aminoethyl)glycine unit, or an analog thereof, as described herein, having a nucleobase (or an analog thereof, as described herein) connected to the central amine thereof, directly or indirectly, e.g., via a methylene carbonyl linkage or variations thereof, as described herein. The N-(2-aminoethyl)glycine units or analogs thereof are connected to one another via an amide bond and form a "peptide-like" backbone chain of the PNA, with the nucleobase or an analog thereof forming a part of a side chain of a backbone unit within the backbone chain. The moiety linking the nucleobase to the backbone unit of the PNA is referred to herein also as nucleobase linkage or nucleobase linking moiety.

A chemical structure of commonly used, N-(2-aminoethyl)glycine-based backbone unit of PNAs is as follows:

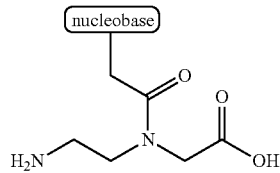

Figure 1:
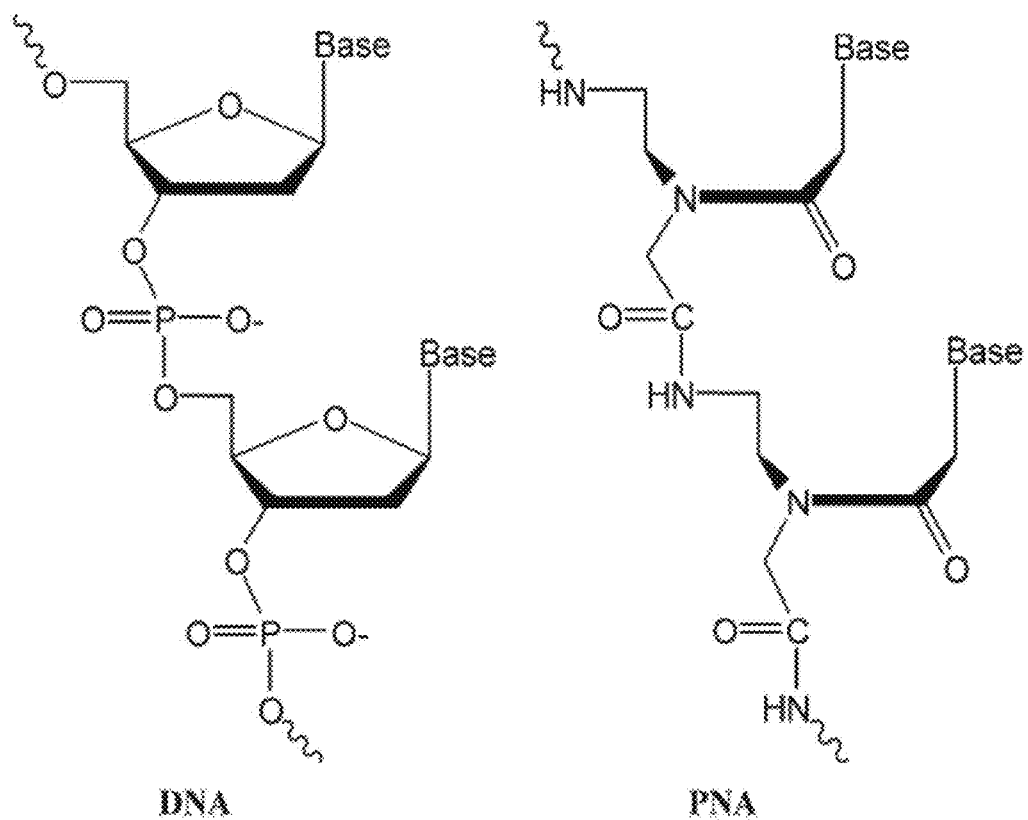

FIG. 1 presents background art PNA structure made of such a backbone unit.

In some embodiments, the term PNA encompasses a modified PNA. The term "modified PNA" encompasses peptide nucleic acid oligomers as described herein, in which one or more of the nucleobase moiety, the "peptide-like" backbone chain and the linkage of the nucleobase to the backbone chain, are analogs of a nucleobase and/or the a N-(2-aminoethyl)glycine unit and/or a methylene carbonyl linkage, respectively, and/or which includes additional appended groups or agents which may be attached to the C- and/or N-terminus or to any other functional group within the backbone chain or nucleobase linkage of the PNA.

Hereinafter, PNAs modified so as to include a backbone unit other than a N-(2-aminoethyl)glycine unit and a nucleobase linkage other than methylene carbonyl are referred to as "backbone-modified PNAs", and PNAs modified by including a nucleobase analog are referred to as "nucleobase modified-PNAs".

The term "modified PNA" also encompasses a molecule that comprises a PNA sequence linked by covalent bond(s) to one or more amino acids or to a sequence of two or more contiguous amino acids, either at a terminus of the PNA or within the backbone chain. A modified PNA can also include a modified C-terminus or N-terminus groups (e.g., an amidated or esterified C-terminus; an acetylated N-terminus, etc.).

The following describes exemplary backbone modified PNAs, which are suitable for use as one or all of the PNAs in the plurality of PNAs as described herein.

I. Backbone modified PNAs in which alkylene (e.g., methylene) group(s) is/are inserted into the PNA backbone and/or the nucleobase linkage. See, for example, Formula I hereinbelow, in which one or both of m and n is greater than 1.

II. Backbone modified PNAs in which methylene or alkylene bridges that connect the various functional groups in the backbone and/or in the nucleobase linkage are introduced. Such a modification typically forms cyclic moieties within the backbone chain. See, for example, Formula I hereinbelow, in which one or both of m and n is optionally greater than 1 and one pair of R1-R5 is joined to form a cyclic ring (e.g., alicyclic or heteroalicyclic ring).

III. Backbone modified PNAs in which one or more amino acid side chains, which can have R or S configuration, are introduced at the α-position of the N-(2-aminoethyl) glycine unit. Any of the naturally-occurring or artificial amino acid side chains are encompassed by this modification. See, for example, Formula II hereinbelow, in which R4 is an amino acid side chain.

IV. Backbone modified PNAs in which one or more amino acid side chains are introduced at the γ-position of the N-(2-aminoethyl) glycine unit. The side chains can have R or S configuration and can be derived from any of the naturally-occurring or artificial amino acid side chains. See, for example, Formula II hereinbelow, in which R3 is an amino acid side chain.

V. Backbone modified PNAs in which one or more of the amide bonds linking the backbone units is replaced by a thioamide bond or any other non-peptide bond such as, for example, carbamate bond, thiocarbamate bond, ester bond, thioester bond, sulfonamide bond, etc.; and/or one or more of the carboxymethylene (methylene carbonyl) nucleobase linkage is replaced by, for example, an alkylene, a thiocarboxymethylene, a carbamate methylene, a thiocarbamate methylene, an amide methylene, a thioamide methylene, a sulfonamide methylene, a sulfonate methylene, an ester methylene, a thioester methylene, etc. See, for example, Formula I or II, in which one or both of Y1 and Y2 is other than C=O.

VI. Backbone modified PNAs in which one or more of the backbone units is/are functionalized by introducing at the α-position, β-position or γ-position of the N-(2-aminoethyl) glycine unit a functional group or moiety such as, for example, a metal-complexing ligand, a receptor ligand, a hydrophobic moiety or group, a negatively or positively charged moiety or group, etc.

A modified PNA, according to some embodiments of the invention, can include one or more of above-mentioned modifications, at any combination.

Exemplary PNAs according to some embodiments of the present invention include one or more backbone units represented by the following general formulae I and II:

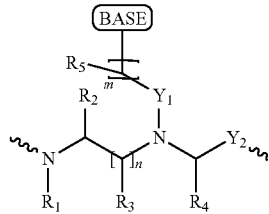

I

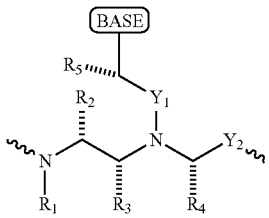

II wherein:
herein throughout, "Base" encompasses a nucleobase or an analog thereof, as described herein;

m and n are each independently an integer from 0 to 4;

$Y_1$ and $Y_2$ are each independently for example, C=O, C=S, CRaRb, C=NRa, C(=O)O, C(=S)O, C(=S)S, C(=O/S)NRa, NRaC(=O/S), O/S—C(=O/S)NRa, NRaC(=O/S)—O/S, S(=O)$_2$, S(=O), S(=O/S)NRa, NRaS(=O/S), etc., with Ra and Rb being each independently, for example, hydrogen, alkyl, aryl or cycloalkyl, each being substituted or not, or, alternatively, Ra, when present, and $R_4$ or $R_5$ or $Y_2$ form together a five-, six- or seven-membered cyclic ring (e.g., cycloalkyl, heretoalicyclic, aryl or heteroaryl;

$R_1$ in Formulae I and II and $R_2$-$R_5$ in Formula I are each independently hydrogen, or any chemical or functional group (e.g., alkyl, cycloalkyl, aryl, heteroaryl, hydroxyl, alkoxy, thiol, thioalkoxy, aryloxy, thioaryloxy, carboxy, amide, thiocarboxy, carbamate, sulfonyl, sulfate, sulfonamide, and any other chemical group; or alternatively, one or more of $R_1$-$R_5$ is a functional moiety such as, for example, a labeling agent, an amino acid side chain, a peptide, a ligand, etc.; or, still alternatively, two or more of $R_1$-$R_5$ are joined together to form a cyclic moiety (e.g., alicyclic (cycloalkyl), heteroalicyclic, aromatic or heteroaromatic); and $R_2$-$R_5$ in Formula II are each a group (e.g., an amino acid side chain or any other functional group or moiety as described herein), which is such that induces chirality to the carbon atoms to which they are attached. These carbon atoms, bearing the $R_2$-$R_5$ groups, can each independently have R or S configuration.

Additional exemplary modified PNA backbone units include, but are not limited to, α-PNAs and alanyl-PNAs, which are based on a polyvaline or polyalanine backbone chains, respectively, or on polyglycin, in which the alpha carbon is substituted by a nucleobase, attached directly or via a linkage as described herein (e.g., formed by the $R_5$—[C]m-$Y_1$ linkage in Formulae I and II) to the alpha carbon.

In some of all of the embodiments described herein for modified PNAs, the modified PNA is such that maintains distances between the nucleobases and rigidity which allow formation of complementary Watson-Crick interactions.

Nucleobase-modified PNAs, which are suitable for use as one or all of the PNAs in the plurality of PNAs as described herein, include PNAs or any of the backbone modified PNAs as described in any of the embodiments herein, in which one or more of the nucleobases is an analog of the five naturally occurring bases (adenine (A), guanine (G), cytosine (C), tymidine (T) and uracil (U)). Thus, such modified PNAs include at least one nucleobase analog.

Exemplary nucleobase analogs can be collectively represented by Formulae III and IV:

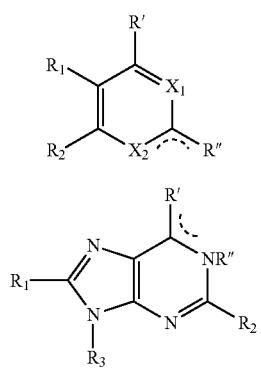

Wherein the dashed lines denote a resonating double bond, such that the moiety between $X_2$ and R" in Formula III can be $X_2$=C—R" or $X_2$—C=R", and the moiety between R' and NR" in Formula IV can be R'=C—NR" or R'—C=N— (with R" being absent.

R' and R" in Formula III can be amine, hydroxyl, thiohydroxy, oxo (=O), thioxo (=S), or absent;

$X_1$ and $X_2$ in Formula I can be N or $CR_4$; and $R_1$-$R_3$ can each independently be hydrogen, or any chemical or functional group (e.g., alkyl, cycloalkyl, aryl, heteroaryl, hydroxyl, alkoxy, thiol, thioalkoxy, aryloxy, thioaryloxy, carboxy, amide, thiocarboxy, carbamate, sulfonyl, sulfate, sulfonamide, and any other chemical group.

Exemplary nucleobase analogs include, but are not limited to, 5-fluorouracil; 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and 3-nitropyrrole.

Exemplary guanine analogs include, but are not limited to, 1-methylguanine, 2,2-dimethylguanine, 2-methylguanine, and 7-methylguanine.

Additional exemplary nucleobase analogs include, for example pseudo-isocytosine (J); 2,6-diaminopurine (D; an analog of adenine); a "guanidine G-clamp" (X, an analog of cytosine); and SU. Exemplary PNAs bearing such nucleobase analogs are depicted as follows:

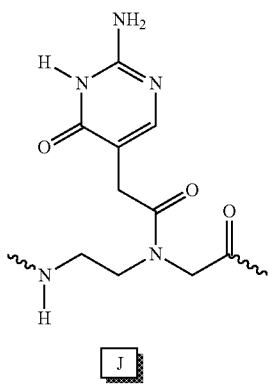

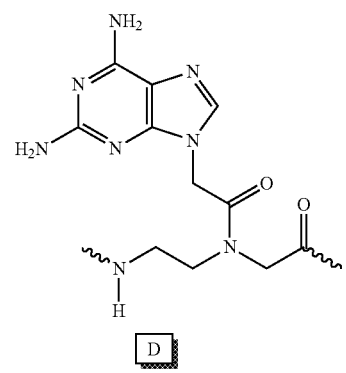

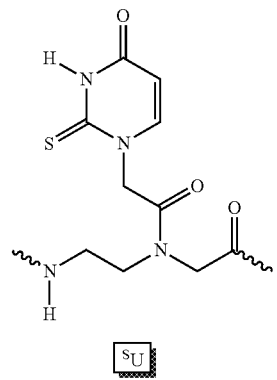

-continued

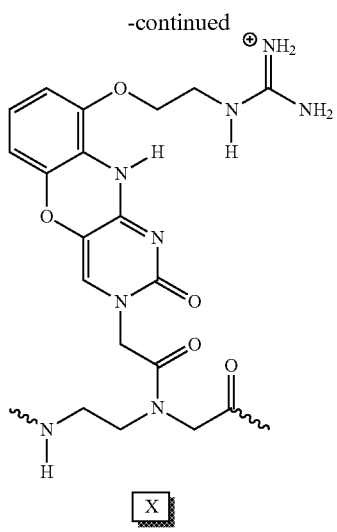

X

These nucleobase analogs can be combined as bases with any of the backbone modified PNAs described herein, including any embodiments thereof.

Any other nucleobase analogs are also contemplated herein, each in combination with PNAs, or with any of the backbone modified PNAs described herein, including any embodiments thereof.

Any of the PNAs and modified PNAs described herein can be synthesized by methods well known in the art using chemistries similar to those used for synthesis of nucleic acids and peptides. PNA backbone units (monomers) used in such syntheses are hybrids of nucleosides and amino acids. PNAs may be synthesized using commercially available reagents and equipment or can be purchased from contract manufacturers. PNA oligomers may also be manually synthesized using either Fmoc or t-Boc protected monomers using standard peptide chemistry protocols. Similarly, standard peptide purification conditions may be used to purify the obtained PNA following synthesis.

The PNAs described herein throughout are denoted by the nucleobase(s) therein (e.g., A, G, C, T, and any combinations thereof), and are presented either in Italics, or as XX-PNA, with "XX" being one or more nucleobases, in order to distinguish from nucleic acids.

Some or all of the PNAs in the plurality of PNAs described in any one of the embodiments herein can be a modified PNA.

The plurality of PNAs described in any one of the embodiments herein can include the same or different PNAs, including differently modified PNAs.

In some of any of the embodiments described herein, at least 80%, or at least 90%, or at least 95%, or at least 99%, or substantially all the PNAs in the plurality of PNAs are the same.

According to some of any of the embodiments of the present invention, one or more, or each of the PNAs in the plurality of PNAs, comprises from 2 to 6 backbone units.

The backbone units in each of the PNAs in the plurality of PNAs can be the same (namely all having a guanine nucleobase or an analog thereof) or different (namely, one or more of the backbone units have a guanine nucleobase or an analog thereof and the other backbone units have one or more nucleobases or analogs thereof other than guanine).

According to some embodiments of the present invention, one or more, or each of the PNAs in the plurality of PNAs, comprises 2 backbone units.

PNA comprising two backbone units is referred to herein also as PNA dimer. The PNA dimer can be a homodimer, of two backbone units each having a guanine nucleobase, or a heterodimer, of one backbone unit having a nucleobase other than guanine, including a guanine analog.

Exemplary PNA dimers useful for forming the composition-of-matter as described herein include, but are not limited to, AG (AG-PNA), CG (CG-PNA), GG (GG-PNA), GA (GA-PNA), GC (GC-PNA), and GT (GT-PNA); with A=adenine-containing PNA backbone unit, C=cytosine-containing PNA backbone unit; G=guanine-containing PNA backbone unit; and T=tymidine-containing PNA backbone unit, and with the abbreviated bases representing the sequence of the backbone units in the PNA from the N-terminus to the C-terminus of the PNA.

In some embodiments, a composition-of-matter formed of a plurality of TG-PNA dimers is excluded from the scope of the present invention.

The Composition-Of-Matter:

In some embodiments, the composition-of-matter as described herein comprises the plurality of PNAs as described in any of the present embodiments, and any combinations thereof, are arranged to form, or are assembled into, an ordered structure.

According to some embodiments, the composition-of-matter described herein exhibits an ordered nanometric or micrometric structure.

By "nanometric structure" it is meant a structure having at least one dimension at the nanoscale (1-1000 nm).

By "micrometric structure" it is meant a structure having at least one dimension at the microscale (1-1000 microns).

By "ordered" structure it is meant that at least 50% of the PNA molecules in the composition-of-matter, preferably at least 80%, 90% or more, form together a structure, having defined shape and dimension, or a plurality of such structures which can be similar (by at least 80%, or by at least 90%, or by at least 95%, or by at least 99%) to one another in shape and dimension. The PNA molecules in an ordered structure as defined herein are not randomly dispersed in the medium in which the structure is generated, but rather are arranged or assembled in an ordered fashion.

In some embodiments, the PNAs self-assemble to generate the ordered structure and hence the ordered structure is also referred to herein as self-assembled (ordered) structure.

The ordered structure of the PNAs as described herein can be in the nanoscale (nanometric) and/or microscale (micrometric), in terms of its dimensions, as defined herein.

In some embodiments, the ordered structure can be generally shaped as one or more of the following:

A generally ribbon-shaped structure or a plurality of generally ribbon-shaped structures which are similar to one another in shape and dimensions, whereby in some embodiments, each ribbon is in the micrometer scale;

A generally-fibrillar structure or a plurality of generally-fibrillar structures which are similar to one another in shape and dimensions, whereby in some embodiments, each fibrillar structure is in the micrometer scale;

A generally spherical structure or a plurality of generally spherical structures, optionally as a cluster or clusters of such generally spherical structures, whereby in some embodiments, each sphere is in the micrometer scale;

A structure generally shaped as a sheet or a plurality of sheets, which are similar to one another in shape and dimensions, whereby the sheet can optionally be a folded sheet (e.g., in a formed of flower-like sheet(s)); and A porous fractal structure or a plurality of fractal structures, whereby the fractal structure can have, for example, a generally spherical shape (e.g., dendritic-like structures or sponge-like porous structures).

As shown in the Examples section that follows, the nature of the ordered structure of the composition-of-matter may be determined or selected, at least in part, on the type and position of the building blocks of the PNA oligomer or dimer. Reference is made in this regard to FIGS. 3A-3C and 4A-4D.

In some embodiments, each of the peptide nucleic acids in the plurality of PNAs forming the structure is an AG-PNA or AG.

In some of these embodiments, the ordered structure is, for example, a generally ribbon-shaped micrometric structure.

In some embodiments, each of the peptide nucleic acids in the plurality of PNAs forming the structure is CG-PNA or CG.

In some of these embodiments, the ordered structure is, for example, a fibrillar micrometric structure.

In some embodiments, each of the peptide nucleic acids in the plurality of PNAs forming the structure is GG-PNA or GG.

In some of these embodiments, the ordered structure is, for example, a clustered spherical micrometric structure.

In some embodiments, each of the peptide nucleic acids in the plurality of PNAs forming the structure is GA-PNA or GA.

In some of these embodiments, the ordered structure is, for example, a flower-like micrometric/nanometric sheet structure.

In some embodiments, each of the peptide nucleic acids in the plurality of PNAs forming the structure is GC-PNA or GC.

In some of these embodiments, the ordered structure is, for example, a fibrillar micrometric structure.

In some embodiments, each of the peptide nucleic acids in the plurality of PNAs forming the structure is GT-PNA or GT.

In some of these embodiments, the ordered structure is, for example, a fractal, sponge-like, porous nanometric/micrometric structure.

Other ordered micrometric and nanometric structures, exhibiting, for example, other shapes, are also contemplated.

In some of any of the embodiments of the present invention, the composition-of-matter consists of the plurality of PNAs, as described herein.

In some of any of the embodiments of the present invention, at least 50% of the plurality of PNAs, as described herein, form, or are arranged to form, an ordered structure as described herein.

In some of any of the embodiments of the present invention, at least 70%, at least 80 5, at least 90%, at least 95%, at least 99%, or essentially all in the PNAs in the plurality of PNAs, as described herein, form an ordered structure as described herein.

In some embodiments, the composition-of-matter consists of the plurality of PNAs, as described herein, in a form of an ordered structure as described herein.

In some embodiments, the ordered structure of the composition-of-matter is other than a monolayer and other than a self-assembled monolayer.

In some embodiments, the ordered structure in the composition-of-matter according to any of the embodiments described herein is generated by contacting the plurality of peptide nucleic acids with an aqueous solution.

In some embodiments, contacting is effected under conditions which favor formation of the ordered structure (e.g., alkaline conditions), as is discussed in further detail under "The process", including any one of the embodiments therein.

According to an aspect of some embodiments of the present invention, there is provided an ordered structure comprising, or being consisted of, self-assembled GC-PNA, as described herein, which exhibits a crystalline structure.

In some of these embodiments, the crystalline structure exhibits features such as hydrogen bond length and distances between bases, as presented in the Examples section that follows, and in FIG. 6A-6F.

Further according to an aspect of some embodiments of the present invention there is provided a process of obtaining the crystalline structure as described herein. The process is effected by contacting the plurality of GC PNAs with a crystallization solution that comprises a bicine buffer, as described in the Examples section that follows.

The Process:

According to an aspect of some embodiments of the present invention, there is provided a process of preparing a composition-of-matter according to any one of the embodiments described herein.

In some embodiments, the process involved generating an ordered structure in any of the compositions-of-matter as described herein.

In some embodiments, the process is effected by contacting the plurality of peptide nucleic acids, as described in any of the respective embodiments, with an aqueous solution.

In some embodiments, the contacting is effected under conditions which favor formation of the ordered structure.

Contacting can be effected for a time period that ranges from milliseconds to minutes, although it may also be effected for hours, and in some cases for days.

Contacting can be effected at a temperature that ranges from 0 to 100° C. In some embodiments, contacting is effected at room temperature, yet any other temperature within the indicated range is also contemplated.

In some embodiments, a concentration of the plurality of peptide nucleic acids in the aqueous solution ranges from about 1 mg/ml to 100 mg/ml, or from about 5 mg/ml to 100 mg/ml, or from about 5 mg/mg to 70 mg/ml, or from about 5 mg/ml to 50 mg/ml, or from 20 mg/ml to 100 mg/ml, or from 30 mg/ml to 100 mg/ml, or from 40 mg/ml to 100 mg/ml, or from 50 mg/ml to 100 mg/ml, or from 50 mg/ml to 80 mg/ml, or from 50 mg/ml to 70 mg/ml, or from 50 mg/ml to 60 mg/ml, including any intermediate value or range.

In some embodiments, the concentration is at least 50 mg/ml, and in some embodiments, it is about 50 mg/ml.

In some embodiments, the aqueous solution has a basic pH, namely a pH greater than 7, or greater than 8, or greater than 9, or greater than 10, or greater than 11 (e.g., pH=12 or greater than 12).

In some embodiments, the aqueous solution comprises a basic buffer, for example, the aqueous solution comprises or is 0.05 M Sodium bicarbonate buffer or a 0.05 M sodium phosphate buffer having pH ranging from 8 to 13.

Other alkaline buffers can also be used.

In exemplary embodiments, the aqueous solution comprises a bicine buffer, 0.1 M. pH 9.0.

In some embodiments, the aqueous solution comprises a polyamine, as discussed in the Examples section that follows. The polyamine may be selected as such that stabilizes the ordered structure and prevents crystallization of salts thereon.

Exemplary polyamines include, without limitation, spermidine, putrescine, diethyleneamine and tris(3-aminopropyl)amine.

In some embodiments, a concentration of the polyamine in the aqueous solution ranges from 0.1-10% v/v and is, for example, 1% v/v.

In some embodiments, the polyamine and its concentration serve for providing an alkaline aqueous solution having a pH as indicated hereinabove.

In some embodiments, contacting is effected for a time period that ranges from a few seconds to a few minutes (e.g., 1-30 minutes, or 1-10 minutes), yet, depending on the concentration of the PNAs, may be effected for longer time periods, such as several hours or days.

As demonstrated in the Examples section using crystallographic measurements, in some embodiments, the ordered structure is formed at an elongation rate of at least 1 micron per second, for example, of 1.2, 1.3, 1.4, 1.5, 1.6, 1.7, 1.8, 1.9, 2, 2.1, 2.2, 2.3, 2.4, 2.5 microns per seconds.

In some embodiments, at least $10^9$ molecules (e.g., at least 1, 1.5, 2., 2.5, 3, 3.2, 3.5, 3.8, $4 \times 10^9$), of the PNAs organize into said ordered structure per second.

In some embodiments, upon contacting the plurality of PNAs with an aqueous solution as described herein and once ordered structures are formed (as can be observed, for example, by electron microscopy such as SEM, or light microscopy), the structures can be isolated from the aqueous solution by e.g., drying.

Fluorescence:

As exemplified in the Examples section that follows, it has been surprisingly uncovered that the PNA-derived ordered structures as described herein are fluorescent per se, namely exhibit fluorescence also in the absence of a material that is associated therewith.

The phrase "fluorescence" refers to emission of light at a certain wavelength during exposure to radiation from an external source (excitation source).

According to some of any of the embodiments described herein, the PNA-based ordered structures and/or a composition-of-matter comprising same as described herein exhibit fluorescence, and in some embodiments exhibit fluorescence with an emission wavelength that depends on the excitation wavelength. Such fluorescence is referred to herein as excitation wavelength-dependent fluorescence.

Thus, in some embodiments, the structures described herein emit light upon excitation, yet, the emitted light correlates to excitation wavelength and moreover, the light is emitted at a wavelength that is shifted upwards with respect to the excitation wavelength.

The difference in wavelength between the apex of the absorption and emission spectra of a fluorescent material is referred to as the Stokes shift of the fluorescent material.

In some embodiments, the excitation wavelength ranges from about 330 nm to about 430 nm.

In some embodiments, the PNA-derived ordered structures are characterized by Stokes shift of from about 20 nm to about 200 nm, or, in some embodiments, of from 50 nm to 100 nm, including any intermediate values and subranges therebetween.

In some embodiments, the shift of the emission wavelength with respect to the excitation wavelength (the aforementioned Stokes shift) decreases with the excitation wavelength. Such a dependence of the Stokes shift on the excitation wavelength is referred to herein as "dynamic Stokes shift." Thus, in various exemplary embodiments of the invention the PNA-derived ordered structures exhibit a dynamic Stokes shift behavior.

In some embodiments, the PNA-derived ordered structures exhibit red edge excitation shift.

A Composition:

According to some embodiments of the present invention a composition-of-matter as described herein is formed in an aqueous solution as described herein and hence, in its final or intermediate form, further comprises the aqueous solution as described in any one of the respective embodiments herein, as used for its preparation.

While in some embodiments, a composition-of-matter as described herein consists essentially of an ordered structure formed of the plurality of PNAs, in some embodiments, there is provided a composition which comprises a composition-of-matter as described herein and an aqueous solution.

In some embodiments, the aqueous solution is as described herein for the process of preparing the composition-of-matter.

According to an aspect of some embodiments of the present invention there is provided a composition which comprises a composition-of-matter as described herein and a material which is in association with the composition-of-matter (e.g., with the ordered structure formed from the PNAs).

The association can be a chemical interaction (e.g., a chemical bond) or a physical interaction (e.g., encapsulation, entrapment, deposition, absorption, etc.).

By "associated therewith" it is meant that the material (e.g., an agent or moiety) is in chemical or physical association with the composition-of-matter or a portion thereof.

Thus, for example, agents or moieties can be attached to the composition-of-matter, by interacting with functional groups present in the PNAs forming the structure via, e.g., covalent bonds, electrostatic interactions, hydrogen bonding, van der Waals interactions, donor-acceptor interactions, aromatic (e.g., π-π interactions, cation-π interactions and metal-ligand interactions. These interactions lead to the chemical association of the agent or moiety to the ordered structure in the composition-of-matter.

As an example, various agents or moieties can be attached to the PNAs forming the structure via chemical interactions with, N-terminus or C-terminus of the PNAs and/or with functional groups on the backbone chain or the nucleobase linkage, if present.

Alternatively, various materials and agents can be attached to the ordered structure by physical association such as magnetic interactions, surface adsorption, encapsulation, entrapment, entanglement and the likes.

The material can be a group or moiety chemically attached to one or more of the backbone units of the PNA or to a terminus thereof, which can be attached to the PNAs prior to formation of the ordered structure or thereafter; or can be a material associated with the ordered structure upon or during its formation, optionally via a functional group or moiety included within the PNA, as described herein, or by absorption, deposition, entrapment or encapsulation.

Exemplary materials include, but are not limited to, a conductor material, a semiconductor material, a thermoelectric material, a magnetic material, a light-emitting material, a labeling agent, a ligand (e.g., a metal binding ligand), a nucleic acid, a polypeptide, a peptide, a biomineral, a polymer, an organic material, a therapeutically active agent (e.g., a drug) and an agent capable of modifying surface properties.

For example, the ordered structures may be in association with conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the ordered structures may enclose, or in association with, for example, silver, gold, copper, platinum, nickel, or palladium. For semiconducting materials the ordered structures may enclose, for example, silicon, indium phosphide, gallium nitride and others.

In another example, the ordered structures may be attached to e.g., carbon nanotubes.

The ordered structures may also encapsulate, or in association with, for example, any organic or inorganic molecules that are polarizable or have multiple charge states. For example, the ordered structures may include main group and metal atom-based wire-like silicon, transition metal-containing wires, gallium arsenide, gallium nitride, indium phosphide, germanium, or cadmium selenide structures.

Additionally, the ordered structure presented herein may enclose, in association with, various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

Specific and representative examples of semiconducting materials which can be encapsulated by the nanostructure presented herein include, without limitation, CdS, CdSe, ZnS and $SiO_2$.

The ordered structure presented herein may also enclose, in association with, a thermoelectric material that exhibits a predetermined thermoelectric power. Preferably, such a material is selected so that the resulting structure composition is characterized by a sufficient figure of merit. Such composition, may be used in thermoelectric systems and devices as heat transfer media or thermoelectric power sources. The thermoelectric material which can be encapsulated in, in association with, the structure of the present invention may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like.

The ordered structures presented herein may also enclose, in association with, magnetic materials. Generally, all materials in nature posses some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by, in association with, the ordered structure of the present embodiments include, without limitation, cobalt, copper, nickel, and platinum. Representative examples of ferromagnetic materials include, without limitation, magnetite and NdFeB.

Other materials which may be encapsulated by, in association with, the ordered structure of the present embodiments include, without limitation, light-emitting materials (e.g., dysprosium, europium, terbium, ruthenium, thulium, neodymium, erbium, ytterbium or any organic complex thereof), biominerals (e.g., calcium carbonate) and polymers (e.g., polyethylene, polystyrene, polyvinyl chloride, polynucleotides and polypeptides).

In some embodiments the material associated with the ordered structure or the composition-of-matter comprising same can be an active agent such as, for example, a surface active agent, a surface modifying agent, a bioactive agent, or can include two or more agents of any combination of the foregoing.

Agents that can be beneficially associated with the structures include, for example, therapeutically active agents, diagnostic agents, biological substances and labeling moieties. More particular examples include, but are not limited to, drugs, cells, proteins, enzymes, hormones, growth factors, nucleic acids, oligonucleotides, nucleic acid intercalators, antisense agents, organisms such as bacteria, fluorescence compounds or moieties, phosphorescence compounds or moieties, and radioactive compounds or moieties.

Surface active agents and surface modifying agents can be, for example, derived from chemical compounds that may modify surface properties of the structures. Such agents include, for example, surfactants, hydrophobic substances such as hydrocarbons being 4-30 carbon atoms in lengths, fatty acids or fatty acyls; carbohydrates; substituted or unsubstituted polyalkylene glycols (PEG), which, when substituted, can include one or more end groups such as, but not limited to, hydroxy, carboxy, alkoxy, amine, amide, hydrazine, thiol, azide, acetylene, acrylate, and any reactive/functional groups; maleimide and biotin/strepavidin.

In some embodiments, the agent is a bioactive agent, as described herein, and can be, for example, a diagnostic agent or a therapeutically active agent.

In some embodiments, the bioactive agent is a diagnostic agent.

As used herein, the phrase "diagnostic agent" describes an agent that upon administration to a body of a subject exhibits a detectable and/or measurable feature. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent agents, phosphorescent agents, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

Hydrogel particles having a labeling moiety associated therewith can be utilized in a variety of applications, including, for example, tracing and tracking the location of the fibrous networks of the present invention in mechanical devices and electronic circuitry; and tracing, tracking and diagnosing concentrations of the hydrogel particles of the present invention in a living tissue, cell or host.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}$Tc, $^{18}$F, $^{131}$I and $^{125}$I.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source (excitation source).

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the bioactive agent is a targeting agent or moiety.

As used herein and in the art, the phrase "targeting agent or moiety" describes a chemical entity which has an affinity to a bodily site such as, for example, to organs or tissues overexpressing a biomolecule (e.g., receptor, enzyme, hormone), or to organs or tissues which are enriched with a chemical or biological moiety (e.g., hydroxyapetite in bone tissues). A targeting moiety can be, for example, a receptor ligand, an enzyme substrate, a bone targeting moiety, a moiety that enhances blood-brain barrier permeability, antibodies or fragments thereof, including monoclonal antibodies, lipoproteins, hormones and artificial analogs thereof, charged molecules, polysaccharides, peptides, nucleic acids (aptamers), small molecules such as, for example, folic acid, biotin, bisphosphonate, vitamins, avidin and/or strepavidin.

In some embodiments, the bioactive agent is a therapeutically active agent.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

The therapeutically active agent can be a small molecule or a biological substance.

As used herein, the phrase "biological substance" refers to a substance that is present in or is derived from a living organism or cell tissue. This phrase also encompasses the organisms, cells and tissues. Representative examples therefore include, without limitation, cells, amino acids, peptides, proteins, oligonucleotides, nucleic acids, nucleic acid intercalators, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

Therapeutically active agents that are suitable for use in the context of some embodiments of the present invention can be small molecules or biomolecules, including, without limitation, anti-proliferative agents, chemotherapeutic agents, radiopharmaceuticals, steroids, vitamins, angiogenesis-promoters, angiogenesis inhibitors, drugs, anti-histamines, antimicrobial agents, antidepressants, anti-psychotic agents, anti-hypertensive agents, anti-inflammatory agents, antioxidants, anti-viral agents, anasthial agents, co-factors, cholesterol, fatty acids, bile acids, saponins, hormones, inhibitors, ligands; cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells.

Some bioactive agents which can be beneficially associated with the structures or composition-of-matter include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially associated with the structures or composition-of-matter include gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Additional bioactive agents which can be beneficially associated with the structures or composition-of-matter include viral and non-viral vectors, such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, skeletal myocytes, macrophage, etc.), replication competent viruses (ONYX-015, etc.), and hybrid vectors, artificial chromosomes and mini-chromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

Any of the active agents described herein can be associated with (e.g., attached to) the structures or composition-of-matter via biostable or biocleavable interactions.

For example, diagnostic agents and targeting agents or moieties are attached to the structures or composition-of-matter by biostable interactions (e.g., biostable chemical bonds), whereby therapeutically active agents are attached to the structures or composition-of-matter via biocleavable bonds or linking moieties, as defined hereinafter.

Any of the compositions-of-matter and compositions as described herein can be used as a part of, or in manufacturing, articles-of-manufacturing or devices, while imparting thereto the unique properties of the PNAs, combined with the properties associated with the ordered structure as described herein, and optionally with properties imparted by the associated material as described herein.

Exemplary such article-of-manufacture or devices include, but are not limited to, a medicament or drug-delivery system (e.g., for releasing the polypeptide, biomineral or therapeutically active agent), a nucleic acid probe, a biosensor, an electrical device, a semiconducting article or device, a thermoelectric article or device, a magnetic article, a light-emitting article or device, a polymeric article, a metallic article or device, and an article or device having activated surface.

Thus, for example, the compositions-of-matter and compositions as described herein can be utilized for DNA or RNA hybridization, in sensitive biosensors; as a scaffold for the formation of metallic assemblies, metallic wires; as a drug delivery agent or system, vesicle for slow drug release, for increasing active surface areas, and for changing surface properties, such as electric properties, optical properties, hydrophobic properties.

The PNA-based structures described herein can be further utilized in forming analogs of DNA assemblies such as DNA origami foldings, four-way DNA junctions and G-quadruplex, with improved intrinsic properties for applications in biotechnology and material science, such as reduced fragility, reduced thermal lability and increased versatility for side-chain functionalization.

The PNA-based self-assembled structures described herein may serve in a variety of technological applications in fields such as material science and bionanotechnology.

For example, the exceptional physical features of the herein disclosed structures may serve as a model for the study of molecular self-assembly and the red edge excitation shift phenomenon; in optical biosensing, organic light-emitting devices (OLEDs), and imaging labels with tunable emission via optical or electrical modulation. The PNA-based structures of the present embodiments can also be used as a fluorescent ink.

The rapid assembly of the PNA-containing building blocks allows to employ these building blocks in motor systems by converting the free energy emitted by the self-assembly process into mechanical motion.

Following is a more detailed description of applications that can benefit from the PNA-based structures according to some embodiments of the present invention.

FIGS. 11A-11C are schematic illustrations of a light emitting system 10, according to some embodiments of the present invention. System 10 can be used for generating light (e.g., responsively to applied voltage) or for converting light (e.g., for shifting the spectrum of the light). In some embodiments of the present invention system 10 serves as an organic light emitting device (OLED).

System 10 comprises a plurality of excitable structures 12.

As used herein "excitable structure" refers to a structure that emits optical radiation in response to an excitation energy delivered thereto.

The term "optical radiation" includes light at any wavelength in the ultraviolet (UV) range, the infrared (IR) range, or the visible range.

Preferably, but not necessarily, structures 12 are organic structures, such as, but not limited to, the PNA-based structures described herein.

System 10 further comprises an excitation system 16 for exciting structures 12 so as to emit light. In various exemplary embodiments of the invention structures 12 emit the light at room temperature (e.g., at about 15-25° C.).

The present embodiments contemplate several types of excitation systems 16 for exciting the structures. Generally, the type of excitation system 16 is selected in accordance with the mechanism by which it is desired to have the light emitted from the structures 12. In various exemplary embodiments of the invention the amount of energy delivered by system 16 to structure 12 is selected in accordance with the desired wavelength of the light that is emitted by structures 12. In some embodiments of the present invention system 10 comprises a controller 26 which controls the amount of energy that is supplied by system 16 to structures 12.

In some embodiments of the present invention controller 26 varies the amount of energy supplied by system 16 to structures 12, in some embodiments of the present invention controller 26 selects the amount of energy supplied by system 16 to structures 12, and in some embodiments of the present invention controller 26 maintains the amount of energy supplied by system 16 to structures 12.

FIG. 2A illustrates an embodiments of the invention in which excitation system 16 comprises a light source 18. In these embodiments, structures 12 emit light via the photoluminescence effect. Light source 18 is preferably a monochromatic light source, e.g., a laser device. In these embodiments, when system 10 comprises controller 26, controller 26 comprises a circuit that controls the wavelength of the light from source 18.

FIG. 2B illustrates an embodiments of the invention in which excitation system 16 comprises or are connectable to a voltage source 20. In these embodiments, structures 12 emit light via the electroluminescence effect. Source 20 can generate electric field by means of electrodes 22. For clarity of presentation, voltage source 20 is illustrated as connected to only one of electrodes 22, but the skilled person would appreciated that more than one electrode can be connected to source 20. In some embodiments of the present invention, electrodes 22 inject holes and electrons to structures 12, in which case structures 12 emit light via injection luminescence. In these embodiments, when system 10 comprises controller 26, controller 26 comprises a circuit that controls the voltage supplied by 20.

The difference between the embodiment in which structures 12 emit light via electroluminescence and the embodiment in which structures 12 emit light via injection luminescence is, inter alia, in the materials from which electrodes 22 are made and/or the voltage level of source 20. For generating light via injection luminescence, electrodes 22 are preferably made of materials having a different work function such that one electrode injects electrons and the other electrode injects holes (or equivalently receives electrons). In this embodiment, the voltage source can be of relatively low voltage since it is not necessary for the generated electric field to be of high intensity. For generating light via electroluminescence, the effect is achieved primarily via application of sufficiently high electric field, in which case the electrodes can be made of the same material.

FIG. 2C illustrates an embodiments of the invention in which excitation system 16 comprises a heat source 24. In these embodiments, structures 12 emit light via the thermoluminescence effect. Preferably, structures 12 in this embodiment incorporate a thermally conductive foreign material as described above for facilitating their electrical communication with heat source 24. In these embodiments, when system 10 comprises controller 26, controller 26 comprises a circuit that controls the amount of heat provided by source 24.

In various exemplary embodiments of the invention structures 12 are deposited on a substrate 14 which can be made of any material, subjected to the luminescence effect by which the structures emit the light.

For example, when structures 12 emit light via the photoluminescence effect, substrate 14 can be made of any material, such as glass, quartz or polymeric material. In this embodiment, substrate can be made of, or being coated by, a material which reflects the light generated by light source 18. Such construction can enhance the photo-excitation.

When structures 12 emit light via the electroluminescence or injection luminescence effect, substrate 14 can be made of an electrically conductive material in which case substrate 14 serves as one of the electrodes 22. Alternatively, electrodes 22 can be deposited directly on substrate 14, in which substrate 14 is preferably made of an electrically isolating material.

When structures 12 emit light via the thermoluminescence effect substrate 14 is preferably made of a thermally conductive material so as to conduct heat from a heat source 24 to structures 12.

FIG. 12 is a schematic illustration of a utility system 40 according to various exemplary embodiments of the present invention. Utility system 40 incorporates system 10, and various other components depending on the application for which system 40 is employed. In some embodiments, utility system 40 is a laser system, in some embodiments, utility system 40 is an active OLED display layer, in some embodiments, utility system 40 is a backlight system for a display, in some embodiments, utility system 40 is an optical communication system, in some embodiments, utility system 40 is an illumination system and in some embodiments, utility system 40 is an optical connector. Such utility systems are known in the art and the skilled person would know how to construct such system using light emitting system 10 of the present embodiments.

FIG. 13 is a more detailed illustration of an OLED 130, according to some embodiments of the present invention. OLED 130 comprises an organic radiation emitting layer 138 disposed between two electrodes, e.g., a cathode 132 and a light transmissive anode 134, formed on a flat sheet, light transmissive substrate 136. Organic radiation emitting layer 138 optionally and preferably comprises excitable organic structures 12 described above. Layer 138 emits light upon application of a voltage across the anode and cathode. Upon the application of voltage from a voltage source V, electrons are directly injected into layer 138 from the cathode 132, and holes are directly injected into layer 138 from the anode 134. The electrons and the holes travel through layer 138 until they recombine to form excited molecules or excitons. The excited molecules or excitons emit optical radiation when they decay. Thus, OLED 130 emits radiation (illustrated by the arrows in FIG. 13) by electron-hole recombination due to direct electron and hole injection into the radiation emitting layer.

FIG. 14 is a schematic illustration of a light emitting system 140 in embodiments in which light conversion is employed. System 140 comprises a light source 142 and a layer 144 of photoluminescent material. At least one of light source 142 and photoluminescent layer 144 comprises the PNA-based structures of the present embodiments. For example, in some embodiments of the present invention light source 142 can be similar to light emitting system 10 or OLED 130. Light source 142 can also be an inorganic light-emitting diode (LED). In some embodiments of the present invention photoluminescent layer 144 comprises the PNA-based structures described herein, and in some embodiments of the present invention photoluminescent layer 144 comprises one or more other photoluminescent materials.

As used herein a photoluminescent material is a material that emits light via any mechanism selected from the group consisting of chemoluminescence, fluorescence and phosphorescence.

Photoluminescent layer 144 is disposed over layer 142 for converting a portion of the light emitted from layer 142 to a different wavelength. In various exemplary embodiments of the invention the density and/or thickness of layer 144 is optionally and preferably selected that a portion of the light from layer 142 is converted by the photoluminescent material, and another portion of the light from layer 142 does not interact with the photoluminescent material and is not converted. The unconverted light mixes with the converted light to form substantially output light of a spectrum that is wider than the each of the emission spectra of layers 142 and 144. For example, the output light can be substantially white.

FIG. 15 is a schematic illustration of a display system 150, according to some embodiments of the present invention. System 150 can serve as an OLED display and optionally also as a light source for a reflective touch screen. System 150 can comprise plurality of light emitting systems 152 arranged in addressable locations over a grid 154. Each of light emitting systems 152 optionally and preferably comprise the PNA-based structures described herein, e.g., as described above with respect to system 10. Each of light emitting systems 152 corresponds to a pixel in display 150, as known in the art of active displays. System 150 also comprises a controller 156 and one or more voltage sources 158. Controller 156 comprises a circuit configured to distribute voltage generated by source 158 to individual light emitting systems 152. In various exemplary embodiments of the invention controller 156 select the voltage level separately for each system 152, such that at least two light emitting systems emit light at different colors, responsively to the different voltage levels applied thereto. In use, controller 156 receives imagery data from an external source of data (not shown) and distributes the voltage among systems 152 to form an image corresponding to the imagery data.

Additional applications (e.g., articles and devices) of the PNA-derived ordered structures described herein, and/or compositions comprising same, are described, for example, in Achim et al., "Peptide Nucleic Acids" in Wiley Encyclopedia of Chemical Biology, 2008, pp. 1-10, and Bonifazi et al., Artificial DNA: PNA & XNA 3:3, 112-122, July-December 2012, which are incorporated by reference as if fully set forth herein.

For example, compositions-of-matter as described herein can be used within articles for purification of nucleic acids; compositions comprising magnetic, semiconductor or conductor materials can be used to construct corresponding articles (e.g., magnetic or electric articles), compositions comprising a metal ligand can be used, in associated with a metal, to form metallic devices for use in various technologies.

It is expected that during the life of a patent maturing from this application many relevant modified PNA and/or nucleobase analogs will be developed and the scope of the terms "PNA" and "nucleobase" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Herein throughout, the phrase "linking moiety" describes a group (a substituent) that is attached to another moiety in the compound via two or more atoms thereof. In order to differentiate a linking group from a substituent that is attached to another moiety in the compound via one atom thereof, the latter will be referred to herein and throughout as an "end group".

As used herein, the term "amine" describes both a —NR'R" group and a —NR'-group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NW-group in cases where the amine is a linking group.

The term "alkyl" describes a saturated aliphatic hydrocarbon including straight chain and branched chain groups. The term "alkylene" describes an alkyl linking group. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain, and is termed alkylene.

The term "cycloalkyl" or "alicyclic" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "amine-oxide" describes a —N(OR')(R") or a —N(OR')— group, where R' and R" are as defined herein. This term refers to a —N(OR')(R") group in cases where the amine-oxide is an end group, as this phrase is defined hereinabove, and to a —N(OR')-group in cases where the amine-oxime is an end group, as this phrase is defined hereinabove.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)-linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)-linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)-linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"-linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

As used herein, the term "methyleneamine" describes an —NR'—CH$_2$—CH=CR"R'" end group or a —NR'—CH$_2$—CH=CR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Materials:

Fmoc-protected PNA monomers were purchased from Polyorg (Leominster, Mass.).

Fmoc-protected PAL-PEG-PS resin was purchased from Life Technologies (Carlsbad, Calif.).

All solvents (peptide grade) used in the synthesis process were purchased from known vendors (e.g., Bio-Lab (Jerusalem, Israel).

All crystallization solutions and equipments were purchased from Hampton Research (Aliso Viejo, Calif.).

PNA Synthesis (General):

PNA dimers (di-PNAs) were synthesized using standard solid-phase protocols, as described in Example 1 hereinbelow.

The crude product was then purified by reversed-phase high performance liquid chromatography (HPLC) using a DIONEX™—UltiMate 3000 instrument equipped with a $C_8$-column, and using TFA 0.1% in acetonitrile 99.9% as a mobile phase. The product was verified by electrospray ionization time-of-flight mass spectrometry (ESI-TOF-MS) [on WATERS®—Q-Tof micro Mass Spectrometer].

Electron Microscopy:

Lyophilized PNA powder was dissolved in e.g., 0.1 M bicine buffer pH 9.0 to a concentration of 50 mg/ml, to thereby form the respective self-assembled structure. The solution was then diluted with ddH$_2$O to a final concentration of 10 mg/ml. A 10 µl aliquot of the self-assembled structures solution was dried at room temperature on a microscope glass cover slip and coated with chromium. Scanning electron microscopy (SEM) images were taken using a JEOL JSM 6700F FE-SEM operating at 10 kV.

TEM measurements were performed on JEOL JEM-1200EX, operating at 80 kV.

Light Microscopy:

Light microscopy was performed using Meiji ML8100 optical microscope.

Crystallization and X-Ray Diffraction Analysis:

The structures forming di-PNAs were screened for crystallization conditions using the hanging-drop vapor-diffusion method on siliconized glass cover slips in Linbro plates, using more than a hundred pre-formulated crystallization solutions. All crystallization experiments were performed at 293 K in a temperature-controlled room. After 5 days colorless needle-like crystals appeared for GC in 0.1 M bicine pH 9.0, 2% v/v 1,4-dioxane, 10% w/v PEG 20,000.

Prior to mounting, crystals were soaked for 1 minute in a cryo-protecting solution (comprising 16% ethylene glycol, 18% sucrose, 16% glycerol, 4% glucose mixed 1:1 ratio with the crystallization reservoir solution). Crystals were mounted on loops and flash frozen in liquid nitrogen for transportation to the synchrotron.

The data were measured at ESRF (European Synchrotron Radiation Facility) beamline ID29 using a Pilatus 6M-F detector and a wavelength of 0.80 Å. A full sphere of 360° of data were collected as 1° frames to a resolution of 0.95 Å. The data were auto-processed using EDNA [Incardona, M. F. et al. *J. Synchrotron Radiat.* 16, 872-879 (2009)]. Two data sets, collected from different locations on the same crystal were merged in XPREP.

The structure was solved by direct methods in SHELXS. The refinements in SHELXL-97 were weighted full-matrix least-squares against |F2| using all data. In the final stages of refinement, SQUEEZE [Spek, A. L. *Acta Crystallogr. D. Biol. Crystallogr.* 65, 148-155 (2009)] was used due to the large voids and remaining disordered solvent molecules.

Atoms were refined independently and non-solvent atoms were refined anisotropically with the exception of hydrogen atoms, which were placed in calculated positions and refined in a riding mode.

Crystal data collection and refinement parameters are given in Table 1 below.

Spectroscopy Measurements:

Emission spectra were taken on a Horiba Jobin Yvon FL3-11 Spectrofluorometer at various excitation wavelengths, as described in FIG. 8B. Emission was recorded between 350 and 600 nm at 25° C. Emission and excitation slits were set at 2.5 nm.

Measurements were performed in a 1 cm rectangular quartz cuvette containing 5 mg/ml of self-assembled di-PNA structures in buffer solution. All spectra were normalized so that the emission maxima and minima are identical.

Fluorescence Imaging:

A fresh solution of 5 mg/ml of self-assembled di-PNA structures was prepared and 10 µl were deposited on a glass slide and covered with a cover slip. Images were acquired using five different excitation/emission filters, as described in FIG. 8A.

Example 1

PNA Syntheses

PNA dimers (di-PNA building blocks) were synthesized using standard solid-phase protocols.

In an exemplary protocol, manual synthesis was performed on Fmoc-PAL-PEG-PS resin). The resin was swollen by stirring with DMF (Biolab) for 2 hours and then filtered.

Cleavage was carried out by 2 cycles of stirring with 20% piperidine (Sigma) in DMF for 15 minutes, followed by filtration. The resin was washed for 2 minutes in DMF, 7 times. Removal of the Fmoc group was confirmed by Kaiser test [Kaiser et al. Analytical biochemistry, 1970. 34(2): p. 595 [45]. Process was repeated if needed.

Desired Fmoc/Bhoc protected PNA monomers (Polyorg inc.), 2.5 equivalents, were dissolved in a DMF and DIEA (Sigma) mixture, 7.5 equivalents, and added to 2.5 equivalents of the resin, in the presence of 2.5 equivalents of HBTU. The coupling mixture was stirred for 2 hours. Coupling was confirmed by Kaiser test (supra). Process was repeated if needed.

The loaded resin with the desired PNA sequence was washed in DCM (Biolab) and methanol (Biolab) and then dried under vacuum. Cleavage of the PNA from the resin and final deprotection were performed with 20% m-cresol (Acros) in TFA (Sigma). The deprotection mixture was kept on ice for 10 minutes and then stirred in room temperature for 90 minutes.

The liquid mixture was separated from the resin by filtration and evaporated under nitrogen stream. Cold diethyl ether (Biolab) was added to the residue and the mixture was centrifuged for 2 minutes at 4,000 rpm. The fluid was removed and the process was repeated 2 more times.

The precipitate was kept under vacuum until completely dry and then kept at −20° C. until use.

Example 2

Formation of Self-Assembled PNA Structures

All the 16 possible di-PNA different combinations were synthesized using solid-phase peptide synthesis as described in Example 1 hereinabove. FIG. 2A presents the different combinations (AA, AC, AG, AT, CA, CC, CG, CT, GA, GC, GG, GT, TA, TC, TG, TT), wherein a PNA is denoted in italics to distinguish it from a nucleic acid.

Each of the 16 di-PNAs was analyzed for its ability to form ordered structures upon dissolving in different solvents, concentrations and conditions.

All procedures were performed at room temperature, and at PNA concentration of 5-100 mg/ml, and in most cases of 50 mg/ml.

Tested solvents included water, ethanol, methanol, DMSO, DMF, HFIP, Sodium carbonate buffer (0.5M), and bicine (2-(Bis(2-hydroxyethyl)amino)acetic acid) buffer (0.1M; pH 9), and sodium phosphate buffer.

The solutions were used to prepare samples for SEM and TEM, optionally upon addition of water to the sample, to a final concentration of 1-10 mg/ml.

Effect of the Di-PNAs on Self-Assembled Structures:

The samples were examined for the presence of ordered structures.

Ordered structures were formed when a solution having basic pH (typically about 12; and 9 for a bicine buffer) were used.

In some of the tested samples, an aqueous solution of a polyamine was used as a basic solution. Such solutions may prevent crystallization of salts over the formed structures.

An exemplary such solution is 1% spermidine in $H_2O$ (v/v). Other exemplary polyamines include putrescine, diethyleneamine and tris(3-aminopropyl)amine). Ordered structures were formed with aqueous solutions (1%) of all of the above-indicated polyamines, and with the above-described bicine buffer.

The following dimers formed ordered structures immediately, in all tested solutions: AG, CG, GA, GC, GG, GT, the chemical structures of which are presented in FIG. 2B. Thus, all PNA dimers that contain the nucleobase guanine, except TG, formed ordered structures.

Images of the self-assembled structures, obtained in SEM measurements, are presented in FIGS. 3A-3C and 4A-4D. As can be seen therein, various ordered structures, including fibrillar structures, ribbon-shaped structures, spherical (optionally clustered) structures, sponge-like porous structures, sheet-based (optionally folded) structures and fractal structures were obtained, depending on the type and position of the nucleobases in the PNA dimer.

More specifically, examination of the solutions using light and electron microscopy, revealed micro-architectures such as long fibers that are tens of microns long for CG and GC PNA dimers (FIGS. 3A-3B), as well as spheroids with a diameter of 2-3 microns for GG (FIG. 3C). PNA dimers of AG, GA, and GT formed ordered structures upon drying the solution (see FIGS. 4A-4C).

All the PNA dimers that formed ordered structures contained a guanine (G) nucleobase.

It is noted that the secondary structure of G-containing PNA oligomers is known to be possibly altered under alkaline conditions, due to deprotonation of the guanine bases [Böjler ET AL. *Nature* 376, 578-581 (1995); Uhlmann et al. *Angew. Chem. Int. Ed.* 37, 2796-2823 (1998)]. It is further noted that guanine is known as a key component in the assembly of various natural nucleic acid structures. Nucleic acid sequences that are rich in guanine are capable of forming G-quadruplexes, the main structural motif of the telomeric DNA. Further, guanosine analogs have been shown to self-associate into dimers, ribbons and macrocycles that can further stack into supramolecular assemblies [Davis, J. T. & Spada, G. P. *Chem. Soc. Rev.* 36, 296-313 (2007)].

To further examine the effect of the guanine nucleobase on the self-assembly of ordered structures, mono-guanine (G) and triple-guanine (GGG) PNAs were prepared and tested. Both these PNAs formed ordered structures at basic aqueous solutions, similar in appearance to those formed by the guanine-containing PNA dimers. See, for example, FIG. 4D.

As a control, the ability of guanine-containing DNA dinucleotides to form ordered assemblies was tested. No formation of ordered dinucleotide structures was observed at all tested conditions.

Effect of pH on Self-Assembled Structures:

Ordered structures were formed when a solution having basic Ph, as described herein, was used.

In some of the tested samples, an aqueous solution of a polyamine was used as a basic solution. Such solutions may prevent crystallization of salts over the formed structures.

An exemplary such solution is 1% spermidine in $H_2O$ (v/v). Another exemplary solution is a bicine buffer as described herein.

FIG. 5 presents light microscopy images of assemblies formed by GC di-PNA upon dissolving in disodium hydrogen phosphate buffer with rising pH levels, and demonstrates the effect of pH on the final structure.

Example 3

Single Crystalline Self-Assembled PNA Structures

The structures-forming di-PNAs were screened for crystallization conditions. Crystals of GC di-PNA were found to grow in a bicine-based crystallization buffer. Since bicine buffer also enables the assembly of ordered structures, it is believed that the crystal structure reflects the solution self-assembled architecture.

The crystal structure of GC, as a representative example, was determined at 0.95 Å resolution with data collected at the European Synchrotron Radiation Facility.

Table 1 below presents the crystal data and structure refinement for the GC di-PNA crystal.

TABLE 1

| PNA | |
|---|---|
| Empirical formula | C21 H27 N13 O6, C2 H6 O2, 2O |
| Formula weight | 651.62 |
| Crystal system | Monoclinic |

TABLE 1-continued

PNA

| | |
|---|---|
| Space group | C2/c |
| a, Å | 33.490(7) |
| b, Å | 20.840(4) |
| c, Å | 17.630(4) |
| α deg | 90.00 |
| β deg | 108.39(3) |
| γ deg | 90.00 |
| V (Å$^3$) | 11676(5) |
| Z | 8 |
| $d_{calc}$ (mg/cm$^3$) | 0.741 |
| μ (mm$^{-1}$) | 0.078 |
| Reflections | 68457 |
| Unique Reflections | 6714 |
| $R_{int}$ | 0.0186 |
| R [I > 2σ (I)] | $R_1$ = 0.0933 $wR_2$ = 0.2528 |
| Goodness of Fit | 1.31 |

$R_1 = \Sigma||F_o| - |F_c||/\Sigma|F_o|$; $wR_2 = \{\Sigma[w(F_o^2 - F_c^2)^2]/\Sigma w(F_o^2)^2]\}^{1/2}$ The determined structure revealed a unique packing for the PNA crystals, as presented in FIGS. 6A-6F. The cytosine and guanine in each molecule form a stacking interaction (see, FIG. 6A).

Then, each molecule forms hydrogen bonds with a neighboring molecule between the cytosine and guanine residues (see, FIG. 6B).

The hydrogen bond length between symmetry related molecules is measured to be 2.85-2.93 Å (see, FIG. 6C), similarly to Watson-Crick base pairing.

The bases are 3.5 Å apart (see, FIG. 6D), as in DNA double helical structures, and do not exhibit any tilt or roll.

Figure 6E:
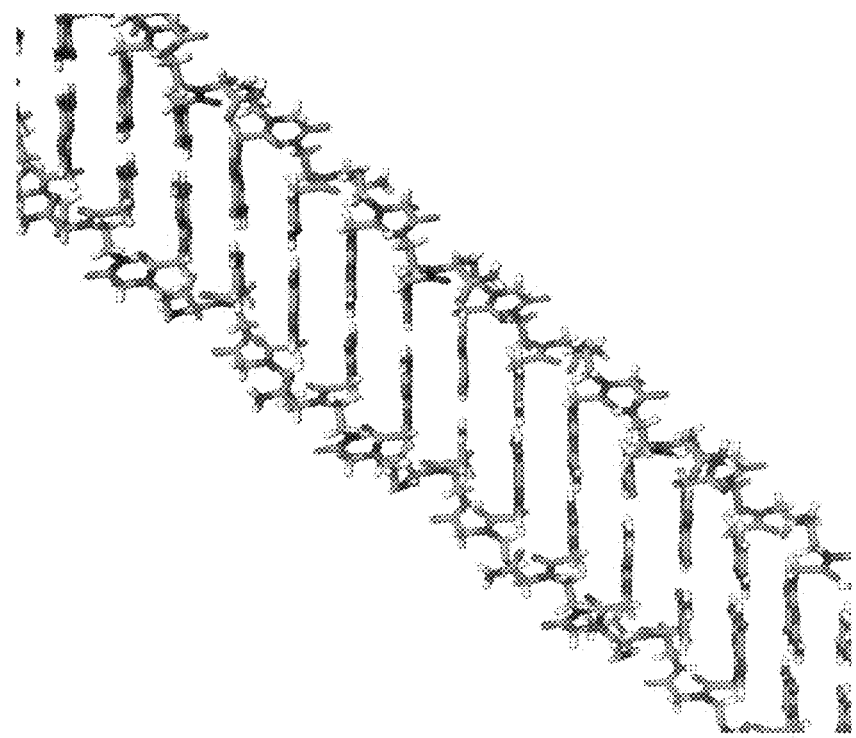

The hydrogen bonding molecules are related to each other via the two-fold dyad that passes between the stacked bases. The packing of the molecule in a centrosymmetric space group is possible due to the non-chiral nature of the polyglycine backbone. The bases are therefore packed in an "infinite" tilted stack through the crystal, as shown in FIG. 6E.

This form of packing results in rectangular-shaped pores comprising over 50% of the crystal volume, as illustrated in FIG. 6F.

The crystal structure reflects the dual identity of PNA. The PNA units form stacking interactions with each other, similarly to aromatic peptides, while at the same time forming the typical Watson-Crick base pairs typical of DNA structures. This unique duality distinguishes these molecules from simple DNA dinucleotides that possess only Watson-Crick base-pairing that did not form any self-assembled structures.

Example 4

Self-Assembly Kinetics

The crystal structure of the self-assembled structures was utilized for estimating the rate by which the PNA dimer building blocks in the solution self-assemble to form the ordered structures.

Briefly, a fresh solution of the PNA building block was dissolved in bicine buffer at a concentration of 5 mg/ml and a single drop was taken and deposited on a glass slide. The drop was monitored using light microscopy and images were captured at a rate of one frame per second.

Snapshots of the captured images, taken every 30 seconds, are presented in FIG. 7A. Small nucleation seeds could be observed within few seconds and continual growth in one axis direction sustained for a few minutes.

To allow better visualization of the structure elongation as a function of time, a recorded video showing one structure growth between frames 26 to 112 was tracked, in which the assembled structure is clearly seen and not overlapped by other architectures (see, FIG. 7B).

The growth rate as measured by the increase in the length of the structure is presented in FIG. 7C, and shows a very good linear fit between the dimension of the assemblies in the long Z-axis and time ($R^2$=0.9975). The calculated elongation rate is 2.23 μm per second. For the imaged structure that is 1.77 μm wide, that translates into a volume increase of approximately 5.5 μm$^3$ per second.

Since the crystal unit cell has a volume of 11,676 Å$^3$ (see Table 1) and contains 8 molecules, it can be estimated that 3.8×10$^9$ di-PNA building block molecules organize into the ordered structures per second.

Example 5

Fluorescence Measurements

During fluorescence measurements, it was surprisingly observed that a sample containing the self-assembled structures described herein exhibits a fluorescence signal similar to that of the same sample, stained with a fluorescence agent, and that fluorescence emission was evident for a wide range of excitation wavelengths. FIG. 8A presents the data obtained for GC di-PNA structures.

FIG. 9 presents the data obtained for CG di-PNA structures prepared in bicine buffer, upon dilution to 5 mg/ml concentration. When excited with UV light the structures emit in blue, when excited with blue light the structures emit in green, when excited with green light the structures emit in red.

Quantitative analyses of the fluorescence of GC di-PNA structures, presented in FIG. 8B, in which fluorescence emission spectra were determined at varied excitation wavelengths, showed that the emission peak is shifted in the direction of the change in excitation.

The consecutive emission maxima as a function of excitation wavelengths were plotted and showed a linear correlation between the excitation and emission peak wavelengths, as shown in FIG. 8C. The 0.7073 slope of the strong fit ($R^2$=0.9943) indicates a dynamic Stokes shift behavior as the distance between the excitation and the emission peaks gradually decreases with longer wavelengths.

Such observed shifts in fluorescence emission in response to shifting the excitation wavelength toward the red edge of the absorption band is termed in the art as red edge excitation shift (REES). The phenomenon was originally described in rigid and highly viscous environments such as low-temperature glasses or highly condensed polymeric states [Demchenko, A. P. The red-edge effect: 30 years of exploration. *Luminesence* 17, 19-42 (2002)]. REES is assumed to be the result of the strong reduction in dynamic environment of excited fluorophores in organized molecular settings. The molecular lattice confinements slow the rates of matrix relaxation and reorientation around the excited state of the fluorophore relative to the fluorescence lifetime [Chattopadhyay, A. & Haldar, S. Dynamic insight into protein structure utilizing red edge excitation shift. *Acc. Chem. Res.* 47, 12-19 (2014)].

In biological and other organic molecules constrains could be imposed by exceptionally ordered hydration shells or rigid membranes. The PNA assemblies disclosed herein, with both stacking and base-pairing as observed in the crystal structure (see, FIGS. 6A-6F), represent a unique state of high polarizability in a motionally restricted environment induced by the condensed lattice packing.

Without being bound to any particular theory, it is assumed that the high stacking interactions exhibited by the di-PNA self-assembled structures described herein accounts for their unique spectral properties.

GC di-PNA structures were further tested for binding DNA intercalators presumably via Watson-Crick base-pairing.

A YOYO-3 intercalator (Life Technologies) was selected in preliminary experiments, since it emits in the red, a region where the PNA emission is lower so it is easy to distinguish between the emission of the PNA and the intercalator.

FIGS. 10A-10B show a bright-field and fluorescence images of a single GC assembly dyed with the intercalator YOYO-3 that exhibits red light emission when bound to nucleic acids, demonstrating the binding of the di-PNA structure to the DNA intercalator.

It is noted that the fluorescence and binding to DNA intercalators as demonstrated herein for representative structures should be exhibited by any of the PNAs described herein, as it derived from the stacking and base-pairing properties that are common to all structures.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of generating a composition-of-matter comprising a plurality of peptide nucleic acids arranged in an ordered nanometric or micrometric structure, each of said peptide nucleic acids independently comprising 1 to 10 backbone units, at least one of said backbone units comprising a guanine nucleobase or an analog thereof, the process comprising contacting said plurality of peptide nucleic acids with an aqueous solution under conditions which favor formation of said ordered nanometric or micrometric structure, said aqueous solution having a pH greater than 8.

2. The process of claim 1, wherein said contacting is such that a concentration of said peptide nucleic acids in said aqueous solution ranges from 10 mg/ml to 100 mg/ml.

3. The process of claim 2, wherein said concentration is about 50 mg/ml.

4. The process of claim 1, wherein each of said peptide nucleic acids independently comprises 2 to 6 of said backbone units.

5. The process of claim 1, wherein each of said peptide nucleic acids comprises 2 of said backbone units and is being a peptide nucleic acid dimer (PNA dimer).

6. The process of claim 5, wherein each of said peptide nucleic acid dimers is independently selected from the group consisting of AG, CG, GG, GA, GC, and GT.

7. The process of claim 5, wherein each of said peptide nucleic acid dimers is AG, and wherein said ordered structure is a ribbon-shaped micrometric structure.

8. The process of claim 5, wherein each of said peptide nucleic acid dimers is CG, and wherein said ordered structure is a fibrillar micrometric structure.

9. The process of claim 5, wherein each of said peptide nucleic acid dimers is GG, and wherein said ordered structure is a clustered spherical micrometric structure.

10. The process of claim 5, wherein each of said peptide nucleic acid dimers is GA, and wherein said ordered structure is a micrometric or nanometric folded sheet structure.

11. The process of claim 5, wherein each of said peptide nucleic acid dimers is GC, and wherein said ordered structure is a fibrillar micrometric structure.

12. The process of claim 5, wherein each of said peptide nucleic acid dimers is GT, and wherein said ordered structure is a fractal porous nanometric or micrometric structure.

13. The process of claim 1, wherein said aqueous solution comprises a buffer having pH greater than 8.

14. The process of claim 1, wherein said aqueous solution comprises a polyamine.

15. The process of claim 14, wherein a concentration of said polyamine in said aqueous solution ranges from 0.1% to 10%, by volume.

16. The process of claim 1, wherein said ordered structure is formed at an elongation rate of at least 1 micron per second.

17. The process of claim 1, wherein at least $10^9$ molecules of said peptide nucleic acids organize into said ordered nanometric or micrometric structure per second.

* * * * *